(12) United States Patent
Shen et al.

(10) Patent No.: US 7,659,296 B2
(45) Date of Patent: Feb. 9, 2010

(54) VITAMIN D RECEPTOR MODULATORS

(75) Inventors: Quanrong Shen, Fishers, IN (US); Alan M. Warshawsky, Carmel, IN (US); Ying Kwong Yee, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 11/721,676

(22) PCT Filed: Dec. 19, 2005

(86) PCT No.: PCT/US2005/046361

§ 371 (c)(1),
(2), (4) Date: Jun. 14, 2007

(87) PCT Pub. No.: WO2006/069154

PCT Pub. Date: Jun. 29, 2006

(65) Prior Publication Data

US 2008/0119407 A1    May 22, 2008

Related U.S. Application Data

(60) Provisional application No. 60/638,029, filed on Dec. 21, 2004.

(51) Int. Cl.
*A61K 31/423* (2006.01)
*C07D 417/02* (2006.01)
*C07D 498/04* (2006.01)
*C07D 263/08* (2006.01)

(52) U.S. Cl. .................. 514/375; 548/217; 548/224; 548/237

(58) Field of Classification Search ............ 548/217, 548/224, 237; 514/375
See application file for complete search history.

(56) References Cited

U.S. PATENT DOCUMENTS

| 2006/0094778 A1 | 5/2006 | Nagpal et al. |
| 2006/0135484 A1 | 6/2006 | Nagpal et al. |
| 2006/0287536 A1 | 12/2006 | Dahnke et al. |
| 2006/0293385 A1 | 12/2006 | Gajewski et al. |
| 2007/0105951 A1 | 5/2007 | Gajewski et al. |
| 2007/0106095 A1 | 5/2007 | Lu et al. |
| 2007/0149810 A1 | 6/2007 | Lu et al. |

FOREIGN PATENT DOCUMENTS

| WO | WO 03/101978 A | 12/2003 |
| WO | WO 2004/048309 A | 6/2004 |
| WO | WO 2005/051893 | 6/2005 |
| WO | WO 2005/051938 A | 6/2005 |
| WO | WO 2006/069153 | 6/2006 |

OTHER PUBLICATIONS

Nagpal, S. et al. "Vitamin D Analogs: Mechanism of Action of Therapeutic Applications", *Curr. Med. Chem.* 2001, 1661-1679, vol. 8.
Bouillon R., et al. Structure-Function Relationships in the Vitamin D Endocrine System, Endocrine Rev. 1995, 200-257, vol. 16.
Swann et al. "Rational Design of Vitamin D3 Analogues Which Selectively Restore Activity to a Vitamin D Receptor Mutant Associated with Rickets" *Org. Lett.* 2002, p. 1863-3866 vol. 4.
Swann et al. "Structure-Based Design of Selective Agonists for a Rickets-Associated Mutant of the Vitamin D Receptor" *J. Am. Chem. Soc.* 2002 13795-13805, vol. 124.

*Primary Examiner*—Kamal A Saeed
*Assistant Examiner*—Samantha L Shterengarts
(74) *Attorney, Agent, or Firm*—James B. Myers

(57) ABSTRACT

The present invention relates to novel, non-secosteroidal, phenyl-benzoxazole compounds of Formula (I) wherein the variables R, R', RP, $RP_3$, $L_{P1}$, $L_{P2}$, ZP, RB, RB', $L_{XB}$ and $Z_{XB}$ are as hereinafter defined, their preparation, pharmaceutical compositions, and methods of use.

11 Claims, No Drawings

VITAMIN D RECEPTOR MODULATORS

REFERENCE TO RELATED APPLICATION

This application is submitted as a United States national phase entry, pursuant to 35 U.S.C. § 371, of PCT/US2005/046361, filed on 19 Dec. 2005, which claims the benefit of U.S. provisional patent application Ser. No. 60/638,029, filed 21 Dec. 2004, each of which is incorporated by reference herein.

BACKGROUND OF THE INVENTION

Vitamin D Receptor (VDR) is a ligand dependent transcription factor that belongs to the superfamily of nuclear hormone receptors. The VDR protein is 427 amino acids, with a molecular weight of ~50 kDa. The VDR ligand, 1α,25-dihydroxyvitamin D3 (the hormonally active form of Vitamin D) has its action mediated by its interaction with the nuclear receptor known as Vitamin D receptor ("VDR"). The VDR ligand, 1α,25-dihydroxyvitamin D3 (1α,25(OH)$_2$D$_3$) acts upon a wide variety of tissues and cells both related to and unrelated to calcium and phosphate homeostasis.

The activity of 1α,25-dihydroxyvitamin D3 in various systems suggests wide clinical applications. However, use of conventional VDR ligands is hampered by their associated toxicity, namely hypercalcemia (elevated serum calcium). Currently, 1α,25(OH)$_2$D$_3$, marketed as Rocaltrol® pharmaceutical agent (product of Hoffmann-La Roche), is administered to kidney failure patients undergoing chronic kidney dialysis to treat hypocalcemia and the resultant metabolic bone disease. Other therapeutic agents, such as Calcipotriol® (synthetic analog of 1α,25(OH)$_2$D$_3$) show increased separation of binding affinity on VDR from hypercalcemic activity.

Chemical modifications of 1α,25(OH)$_2$D$_3$ have yielded analogs with attenuated calcium mobilization effects (R. Bouillon et. al., Endocrine Rev. 1995, 16, 200-257). One such analog, Dovonex® pharmaceutical agent (product of Bristol-Meyers Squibb Co.), is currently used in Europe and the United States as a topical treatment for mild to moderate psoriasis (K. Kragballe et. al., Br. *J. Dermatol.* 1988, 119, 223-230).

Other Vitamin D$_3$ mimics have been described in the publication, *Vitamin D Analogs: Mechanism of Action of Therapeutic Applications*, by Nagpal, S.; Lu, J.; Boehm, M. F., *Curr. Med. Chem.* 2001, 8, 1661-1679.

Although some degree of separation between the beneficial action and calcium raising (calcemic) effects has been achieved with these VDR ligands, to date the separation has been insufficient to allow for oral administration to treat conditions such as osteoporosis, cancers, leukemias, and severe psoriasis.

One example of a major class of disorder that could benefit from VDR mediated biological efficacy in the absence of hypercalcemia is osteoporosis. Osteoporosis is a systemic disorder characterized by decreased bone mass and microarchitectural deterioration of bone tissue leading to bone fragility and increased susceptibility to fractures of the hip, spine, and wrist (World Health Organization WHO 1994). Osteoporosis affects an estimated 75 million people in the United States, Europe, and Japan.

Within the past few years, several antiresorptive therapies have been introduced. These include bisphosphonates, hormone replacement therapy (HRT), a selective estrogen receptor modulator (SERM), and calcitonins. These treatments reduce bone resorption, bone formation, and increase bone density. However, none of these treatments increase true bone volume nor can they restore lost bone architecture.

Another major disorder that could benefit from VDR mediated biological activity is psoriasis. Psoriasis is one of the most common dermatologic diseases and is a chronic inflammatory skin condition characterized by erythematous, sharply demarcated papules and rounded plaques, covered by silvery micaceous scale.

Synthetic VDR ligands with reduced calcemic potential have been synthesized. For example, a class of bis-phenyl compounds stated to mimic 1α,25-dihydroxyvitamin D$_3$ is described in U.S. Pat. No. 6,218,430 and the article; "Novel nonsecosteroidal vitamin D mimics exert VDR-modulating activities with less calcium mobilization than 1α,25-Dihydroxyvitamin D$_3$", by Marcus F. Boehm, et. al., *Chemistry & Biology* 1999, Vol 6, No. 5, pgs. 265-275.

Synthetic VDR ligands having an aryl-thiophene nucleus are described in U.S. provisional patent application Ser. No. 60/384,151, filed 29 May 2002 (WO 03/101,978), and synthetic VDR ligands having aryl-napthaline nucleus are described in U.S. provisional patent application Ser. No. 60/637,930 filed 21 Dec. 2004.

There remains a need for improved treatments using alternative or improved pharmaceutical agents that mimic 1α,25-dihydroxyvitamin D$_3$ to stimulate bone formation, restore bone quality, and treat other diseases without the attendant disadvantage of hypercalcemia.

SUMMARY OF THE INVENTION

Novel compounds having a phenyl-benzoxazole nucleus of Formula "(XP)" have been found effective as Vitamin D Receptor modulators (VDRM):

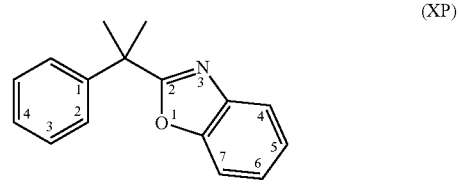

Compounds of the invention with VDR modulating activities are represented by Formula (I)

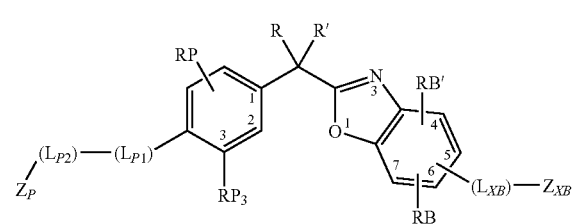

wherein the variables R, R', RP, RP$_3$, L$_{P1}$, L$_{P2}$, Z$_P$, RB, RB', L$_{XB}$ and Z$_{XB}$ are as hereinafter defined.

In another aspect, the present invention is directed towards pharmaceutical compositions containing pharmaceutically effective amounts of compounds of Formula I or a pharmaceutically acceptable salt or a prodrug thereof, either singly or in combination, together with pharmaceutically acceptable carriers and/or auxiliary agents.

Another aspect of the invention is a pharmaceutical formulation for treatment or prevention of osteoporosis containing pharmaceutically effective amounts of the vitamin D receptor modulator compound of Formula I alone or together with pharmaceutically effective amounts of co-agents conventionally used for the treatment of osteoporosis.

Another aspect of the invention is a pharmaceutical formulation for treatment or prevention of psoriasis containing pharmaceutically effective amounts of the vitamin D receptor modulator compound of Formula I alone or together with pharmaceutically effective amounts of co-agents conventionally used for the treatment of psoriasis.

Another aspect of the invention is a pharmaceutical formulation for treatment or prevention of prostate cancer containing pharmaceutically effective amounts of the vitamin D receptor modulator compound of Formula I alone or together with pharmaceutically effective amounts of co-agents conventionally used for the treatment of prostate cancer.

Another aspect of the invention is to use the compounds of Formula I to treat disease states responsive to Vitamin D receptor ligands.

Another aspect of the invention is the prevention and treatment of acne, actinic keratosis, alopecia, Alzheimer's disease, autoimmune induced diabetes, benign prostatic hyperplasia, bladder cancer, bone fracture healing, breast cancer, Crohn's disease, prostate cancer, colon cancer, Type I diabetes, host-graft rejection, hypercalcemia, Type II diabetes, leukemia, multiple sclerosis, insufficient sebum secretion, osteomalacia, osteoporosis, insufficient dermal firmness, periodontal disease, insufficient dermal hydration, myelodysplastic syndrome, psoriatic arthritis, psoriasis, renal osteodystrophy, rheumatoid arthritis, scleroderma, seborrheic dermatitis, skin cancer, systemic lupus erythematosis, skin cell damage from mustard vesicants, ulcerative colitis, and wrinkles, by administering to a mammal in need thereof a pharmaceutically effective amount of a compound of Formula I.

DETAILED DESCRIPTION OF THE INVENTION

Definitions

The term, "abscess" refers to adverse complications often associated with surgery, trama, or diseases that predispose the host to abscess formation from encapsulated bacteria lymphocytes, macrophages, and etc.

The term, "adhesion" refers to the adverse and abnormal union of surfaces normally separate by the formation of new fibrous tissue resulting from an inflammatory process.

The term, "compound of the invention" refers to a compound represented by Formula I or as set out as products of the Examples or synthesis schemes described herein.

The term, "Active Ingredient" means a compound of the invention.

The term, "mustard" is inclusive of both sulfur mustards and nitrogen mustards, either alone or in any combination. Examplary of such compounds are the vesicants; bis(2-chloroethyl) sulfide (Chemical Agent Symbol HD), $Cl(CH_2)_2S(CH_2)_2Cl$ 1,2-bis(2-chloroethylthio)ethane (Chemical Agent Symbol Q), $Cl(CH_2)_2S(CH_2)_2S(CH_2)_2Cl$; bis(2-chloroethylthioethyl)ether, $Cl(CH_2)_2S(CH_2)_2O(CH_2)_2S(CH_2)_2Cl$ (Chemical Agent Symbol T); tris(2-chloroethyl) amine (Chemical Agent Symbol HN3) $N(CH_2CH_2Cl)_3$; N-methyl-2,2'-dichlorodiethylamine (Chemical Agent Symbol NH2); and 2,2'-dichlorotriethylamine, $CH_3CH_2N(CH_2CH_2Cl)_2$ (Chemical Agent Symbol NH1).

The term heteroaryl as used herein refers to the heteroaryls illustrated below:

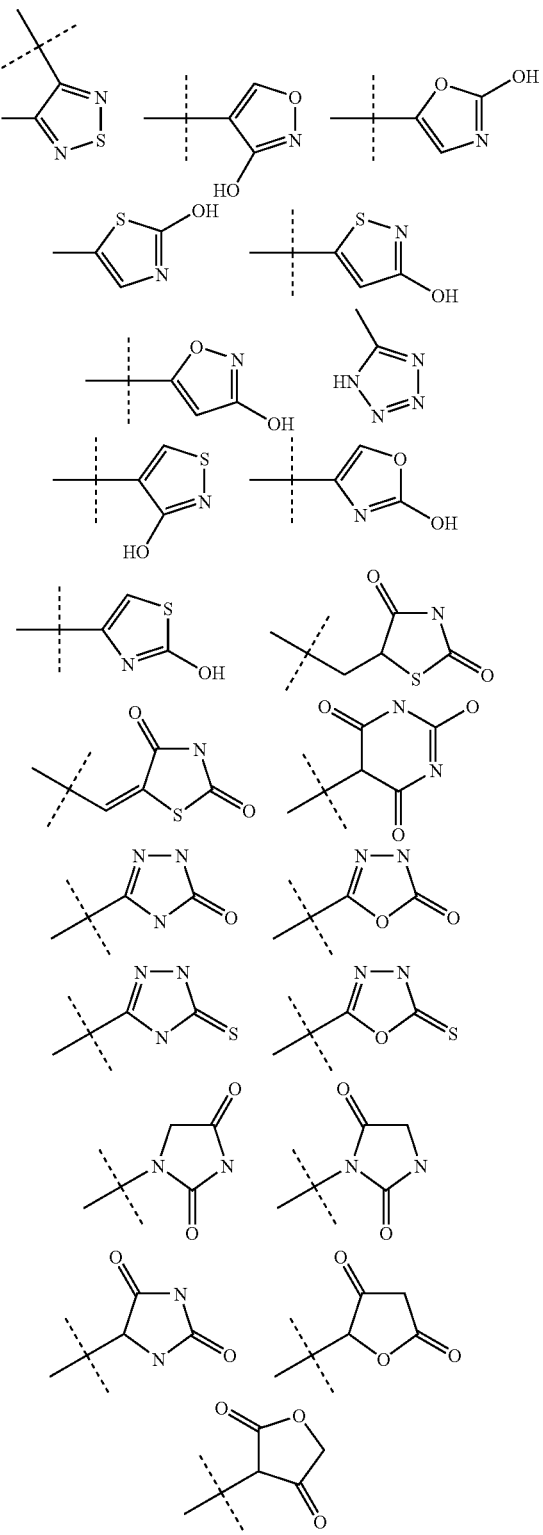

where the dotted line crossing a solid line symbol represents a bond of attachment between the atom of the radical and the rest of the molecule.

The term, "(Acidic Group)" means an organic group that acts as a proton donor capable of hydrogen bonding. Illustrative of an (Acidic Group) is a group selected from the following: carboxylic acid, acylsulfonamide, tetrazolyl, substituted heteroaryls with acidic hydrogens, i.e., hydroxyl groups.

The term, "mammal" includes humans.

The terms "halo" and halogen refer to fluorine, chlorine, bromine, and iodine. Preferred halogens for the present invention include fluorine.

Unless specified herein, chemical terms are used in their customary usuage as understood by one skilled in the art.

The term, "$C_{1-3}$ alkyl" refers to an alkyl group selected from methyl, ethyl, n-propyl, and isopropyl. The abbreviations, "Me" means methyl; "Et" means ethyl; "iPr" or "i-Pr" means 1-methylethyl; and "tBu" or "t-Bu" means 1,1-dimethylethyl. The alkyl group whether used singularly or in conjunction with other substituent(s) is attached to the referenced compound through a carbon atom of the alkyl group.

The term, "branched $C_3$-$C_5$ alkyl" is an alkyl group selected from 1-methylethyl; 1-methylpropyl; 2-methylpropyl; 1,1-dimethylethyl; 1,1-dimethylpropyl; 1,2-dimethylpropyl; or 2,2-dimethylpropyl. Preferred branched $C_3$-$C_5$ alkyl groups are 2-methylpropyl and 1,1-dimethylethyl, with the 1,1-dimethylethyl group being most preferred.

The term "alkenyl" refers to aliphatic groups wherein the point of attachment is a carbon-carbon double bond, for example vinyl, 1-propenyl, and 1-cyclohexenyl. Alkenyl groups may be straight-chain, branched-chain, cyclic, or combinations thereof, and may be optionally substituted. It will be understood that alkenyl groups can include one or more double bonds. Further, the alkenyl groups can include positional isomers about the double bonds i.e. trans (Z) or cis (E) isomers. Suitable alkenyl groups have from 2 to about 20 carbon atoms.

The term "$C_1$-$C_5$ alkyl" refers to saturated aliphatic groups including straight-chain, branched-chain, and cyclic groups and any combinations thereof. Examples of $C_1$-$C_5$ alkyl groups are methyl, ethyl, n-propyl, from 1-methylethyl; n-butyl, 1-methylpropyl; 2-methylpropyl; 1,1-dimethylethyl; n-amyl, 1,1-dimethylpropyl; 1,2-dimethylpropyl; and 2,2-dimethylpropyl.

The term "cycloalkyl" includes organic radicals having 3 to 8 carbon atoms as ring members. Examples include: cyclopropyl, cyclobutyl, cyclopentyl and cyclohexyl. When substituted, the substituents can be selected from halo, hydroxyl, —CN, $C_1$-$C_3$ alkyl, —SH, —O$C_1$-$C_3$ alkyl, and —S$C_1$-$C_3$ alkyl.

The term, "cycloalkenyl" includes organic radicals having 3 to 8 carbon atoms as ring members; non-limiting examples include: cyclopropenyl, cyclobutenyl, cyclopentenyl and cyclohexenyl.

The term, "$C_1$-$C_5$ haloalkyl" is an alkyl group containing one or more halogen atoms. The term, "$C_1$-$C_5$ fluoroalkyl" is an alkyl group containing fluorine and includes organic radicals such as —CF$_3$, —CHF$_2$, —CH$_2$F, —CF$_2$CF$_3$, —CHFCF$_3$, —CH$_2$CF$_3$, —CH$_2$CHF$_2$, and —CH$_2$CH$_2$F, with —CF$_3$ being preferred.

The term, "hydroxyalkyl" means an alkyl group having at least one hydroxyl group. Non-limiting examples include: 3-methyl-3-hydroxypentyl, 3-methyl-3-hydroxypentenyl, 3-methyl-3-hydroxypentynyl, 3-ethyl-3-hydroxypentyl, 3-ethyl-3-hydroxypentenyl, 3-ethyl-3-hydroxypentynyl, 3-ethyl-3-hydroxy-4-methylpentyl, 3-ethyl-3-hydroxy-4-methylpentenyl, 3-ethyl-3-hydroxy-4-methylpentynyl, 3-propyl-3-hydroxypentyl, 3-propyl-3-hydroxypentenyl, 3-propyl-3-hydroxypentynyl, 1-hydroxy-2-methyl-1-(methylethyl)propyl, 2-methyl-3-hydroxy-4,4-dimethylpentyl, 2-methyl-3-hydroxy-3-ethylpentyl, 2-ethyl-3-hydroxy-3-ethylpentyl, 2-ethyl-3-hydroxy-4,4-dimethylpentyl, 1-hydroxycycloalkenyl; and 1-hydroxycycloalkyl.

The term "hydroxycycloalkyl" refers to a radical having the general structural formula:

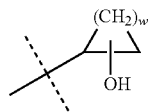

where w is an integer from 1 to 6 and the hydroxyl radical is substituted on any ring carbon atom. Examples include: 2-hydroxycyclohexylmethyl, 3-methyl-2-hydroxycyclohexyloxy, 3-methyl-2-hydroxycyclohexylmethyl, and 3,3-dimethyl-2-hydroxycyclohexyloxy.

The term "1-hydroxycycloalkyl" refers to a radical having the general structural formula:

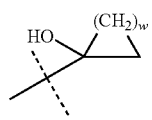

where w is defined as above. Examples of 1-hydroxycloalkyl radicals include: 1-hydroxycyclopropyl, 1-hydroxycyclobutyl, 1-hydroxycyclopentyl, 1-hydroxycyclohexyl, 1-hydroxycycloheptyl, and 1-hydroxycyclooctyl.

The term oxocycloalkyl refers to a radical having the general structural formula:

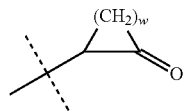

where w is defined as above. The bond of attachment of the oxocycloalkyl to the referenced molecule need not be restricted to the carbon adjacent to the carbonyl carbon, but can be attached via any of the carbon atoms making up the ring. Non limiting examples of oxocycloalkyl radicals include: 2-oxocyclohexyloxy, 2-oxocyclohexylmethyl, 3-methyl-2-oxocyclohexyloxy, 3-methyl-2-oxocyclohexylmethyl, 3,3-dimethyl-2-oxocyclohexyloxy, 3,3-dimethyl-2-oxocyclohexylmethyl, and 2-hydroxycyclohexyloxy.

Certain compounds of the invention exist in isomeric configurations with chiral centers, i.e., diastereomers and enantiomers. Each of the isomeric forms of the compounds are contemplated to be within the scope of the present invention. Each of the various isomers can be prepared as single isomers and/or separated into single isomers by techniques known to those skilled in the art. Therefore, the compounds of the present invention can be used either as single isomer or isomeric form or alteneratively the compounds of the present invention can be used as a combination of isomers. The "jagged" bond illustrated below is used to represent that carbon to which it is attached can exist as either configuration, i.e., R or S.

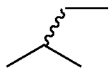

It also will be understood by thoses skilled in the art that compounds of the present invention can exist in two or more tautomeric forms. All such automeric froms are contemplated to be included within the scope of the present invention.

Compounds of the Invention:

The compounds of the invention with vitamin receptor modulating (VDRM) activity are represented by Formula (I) or a pharmaceutically acceptable salt or a prodrug derivative thereof:

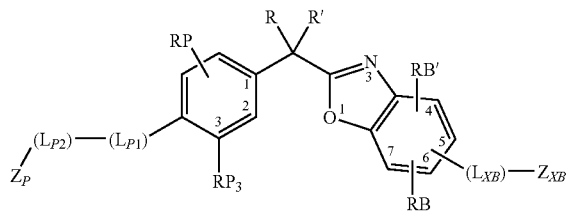

I wherein

R and R' are independently $C_1$-$C_5$ alkyl, $C_1$-$C_5$ haloalkyl, or together R and R' form a substituted or unsubstituted, saturated or unsaturated cycloalkyl ring having from 3 to 8 carbon atoms;

$RP_3$ and RB are independently selected from the group consisting of hydrogen, halo, $C_1$-$C_5$ alkyl, $C_1$-$C_5$ haloalkyl, —O—$C_1$-$C_5$ alkyl, —S—$C_1$-$C_5$ alkyl, —O—$C_1$-$C_5$ haloalkyl, —CN, —NO$_2$, acetyl, —S—$C_1$-$C_5$ haloalkyl, $C_2$-$C_5$ alkenyl, $C_3$-$C_5$ cycloalkyl, and $C_3$-$C_5$ cycloalkenyl;

RP and RB' are independently selected from: hydrogen, halo, $C_1$-$C_5$ alkyl, $C_1$-$C_5$ haloalkyl, —O—$C_1$-$C_5$ alkyl, —S—$C_1$-$C_5$ alkyl, —O—$C_1$-$C_5$ haloalkyl, —CN, —NO$_2$, acetyl, —S—$C_1$-$C_5$ haloalkyl, $C_2$-$C_5$ alkenyl, $C_3$-$C_5$ cycloalkyl, or $C_3$-$C_5$ cycloalkenyl;

($L_{P1}$), ($L_{P2}$), and ($L_{XB}$) are divalent linking groups independently selected from the group consisting of: a bond, —(CH$_2$)$_m$—C(OH)—, (CH$_2$)$_m$—O—, —(CH$_2$)$_m$—S—, —(CH$_2$)$_m$—S(O)—, —(CH$_2$)$_m$—S(O)$_2$—, —(CH$_2$)$_n$—N(R40)-, —(CH$_2$)$_m$—C(R40)(R41)-, —(CH$_2$)$_m$—C(O)—, —N(R40)-C(O)—, —(CH$_2$)$_m$—CH=CH—, and —(CH$_2$)$_n$—C≡C—;

where m is 0-5;

R40 and R41 each is independently selected from: hydrogen, $C_1$-$C_5$ alkyl, $C_1$-$C_5$ hydroxyalkyl, $C_1$-$C_5$ haloalkyl, $C_2$-$C_5$ alkenyl, $C_3$-$C_5$ cycloalkyl, $C_3$-$C_5$ cycloalkenyl;

$Z_P$ is selected from: branched $C_3$-$C_5$ alkyl, $C_3$-$C_{10}$ hydroxyalkyl, $C_3$-$C_{10}$ hydroxyalkenyl, $C_3$-$C_{10}$ hydroxyalkynyl, $C_3$-$C_{10}$ hydroxycycloalkyl, $C_4$-$C_{10}$ hydroxy cycloalkenyl, and oxocycloalkyl;

$Z_{XB}$ is selected from: $C_1$-$C_5$ alkyl, $C_2$-$C_5$ alkenyl, $C_3$-$C_5$ cycloalkyl, $C_3$-$C_5$ cycloalkenyl, $C_1$-$C_5$ hydroxyalkyl, $C_1$-$C_5$ haloalkyl, $C_1$-$C_5$ alkylaryl, $C_1$-$C_5$ hydroxyalkylaryl, $C_0$-$C_5$ alkyl-CO$_2$H, $C_0$-$C_3$ alkyl-cycloalkyl-CO$_2$H, $C_0$-$C_3$ alkyl(cycloalkyl)C(O)NHSO$_2$Me, $C_0$-$C_3$ alkyl(cycloalkyl)C(O)NH-heteroaryl, $C_0$-$C_3$ alkyl(cycloalkyl)NHSO$_2$($C_1$-$C_5$ alkyl), $C_0$-$C_5$ alkyl-N(R40)(R41), —X—($C_1$-$C_5$ alkyl), —X—($C_1$-$C_5$ alkenyl), —X—($C_3$-$C_5$ cycloalkyl), —X—($C_3$-$C_5$ cycloalkenyl), —X—($C_1$-$C_5$ haloalkyl), —X—($C_1$-$C_5$ hydroxyalkyl), —X—($C_1$-$C_5$ alkylaryl), —X(OC$_1$-$C_5$ alkyl), —XN(R40)(R41), —XN(R40)aryl, —N(CH$_3$)(OCH$_3$), —N(OH)(CH$_3$), —N(R42)-($C_1$-$C_5$ alkyl)CO$_2$H, —N(R42)-($C_1$-$C_5$ alkyl)C(O)($C_1$-$C_5$ alkyl), —N(R42)-($C_1$-$C_5$ alkyl)C(O)(OC$_1$-$C_5$ alkyl), —N(R42)-SO$_2$—($C_1$-$C_5$ alkyl), —NR(42)-S(O)—($C_1$-$C_5$ alkyl), —P(O)—(OC$_1$-$C_5$ alkyl)$_2$, heteroalkyl, heteroaryl, and —N=C(R40)N(R40)(R41);

R42 is selected from: H, $C_1$-$C_3$ alkyl; and $C_1$-$C_3$ haloalkyl;

X is selected from: O, C(O), C(S), S(O), and SO$_2$;

provided that RB is substituted at either the 6 or 7 position of the benzoxazole ring, except that RB is substituted only at the 7 position of the benzoxazole ring when $Z_{XB}$ is at the 6 position; and provided that -($L_{XB}$)-$Z_{XB}$ is substituted at either the 5 or 6 position of the benzoxazole ring; and provided that RB is substituted at either the 6 or 7 position of the benzooxazole ring, except that RB is substituted only at the 7 position of the benzoxazole ring when the group -($L_{XB}$)-$Z_{XB}$ is at the 6 position; and provided that RB' is substituted at either the 4 or 5 position of the benzoxazole ring, except that RB' is substituted only at the 5 position of the benzoxazole ring when the group -($L_{XB}$)-$Z_{XB}$ is at the 6 position of the phenyl ring; and provided that RP is substituted at either the 2, or 5 or 6 position of the phenyl ring; or a pharmaceutically acceptable salt, solvate, prodrug, enantiomer, racemate, diastereomer or mixture of diastereomers thereof.

It will be understood by those skilled in the art that the individual groups listed herein for the divalent linkers, ($L_{P1}$), ($L_{P2}$), and ($L_{XB}$), can be attached at either end to the benzoxazole nucleus. For example, for the linking group, —N(R40)-C(O)—, either the nitrogen can be attached to the benzoxazole nucleus or, alternatively, the carbonyl carbon can be attached to the benzoxazole nucleus.

In preferred embodiments, compounds of the invention include the compounds of Formula I having as preferred substituents;

R and R' are independently methyl or ethyl;

RP is hydrogen or methyl;

$RP_3$ and RN are independently hydrogen, methyl, ethyl, —O-methyl, or cyclopropyl;

($L_{P1}$) is a bond;

($L_{P2}$) is a bond, —CH$_2$—, —CH(OH)—, or —C(Me)OH—;

($L_{XB}$) is a bond, —C(O)—, —C(O)NH—, or —C(O)N(Me)—

$Z_P$ is 1,1-dimethylethyl, 1-hydroxycyclopentyl, 1-hydroxycyclohexyl, 3-ethyl-3-hydroxypentyl, 3-ethyl-3-hydroxypentenyl, and 3-ethyl-3-hydroxypentynyl;

$Z_{XB}$ is —CO$_2$H, —CO$_2$(R40), —N(R40)(R41), NH—C(Me)(OH)—C(O)OH, —C(O)NMe—CH$_2$—C(O)OH, —C(O)NMe—CH$_2$—C(O)OMe, —C(O)NMe—CH$_2$—C(O)OEt, —C(O)NMe—CH$_2$—C(O)OiPr, —C(O)NMe—CH$_2$—C(O)tBu, -cycloalkyl-C(O)OH, —C(O)NMe—C(Me)$_2$—C(O)OH, —C(O)N(R40)S(O)(R42), —C(O)N(R40)SO$_2$R42, —C(O)—5-tetrazolyl, —C(O)N(R40)-($C_1$-$C_5$ alkyl)-S(O)R42, —C(O)N(R40)-($C_1$-$C_5$ alkyl)-S(O)$_2$R42, and —CH$_2$CO$_2$H.

Particularly preferred compounds of the invention and salts and prodrug derivatives are represented by formulae C1 to C16 as follows:
C1)
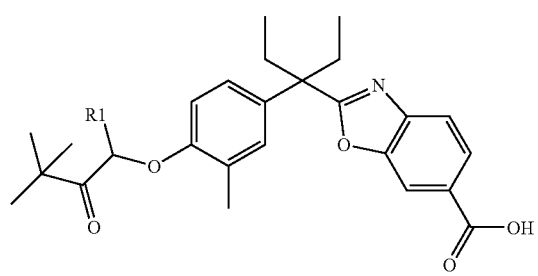
C2)
C3)
C4)
C5)
-continued
C6)
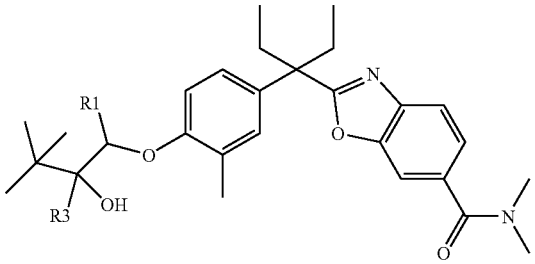
C7)
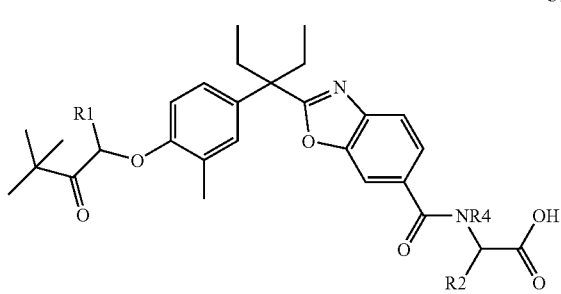
C8)
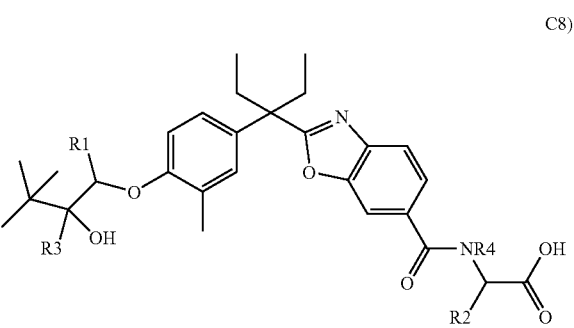
C9)
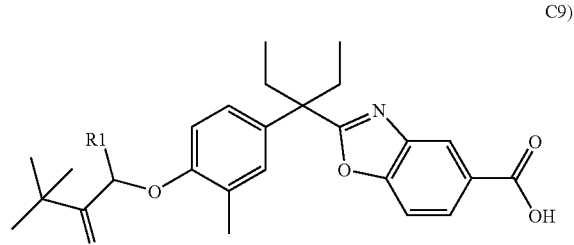
C10)
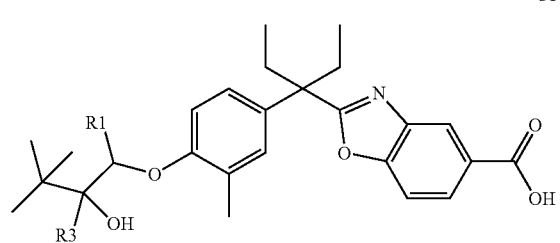

-continued

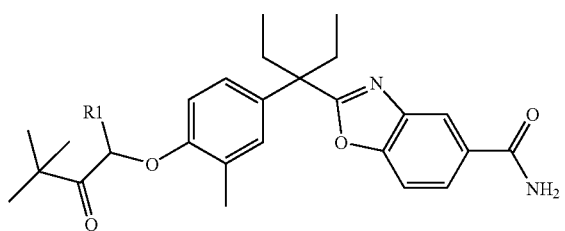

C11)

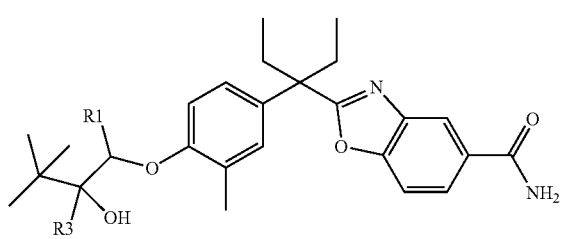

C12)

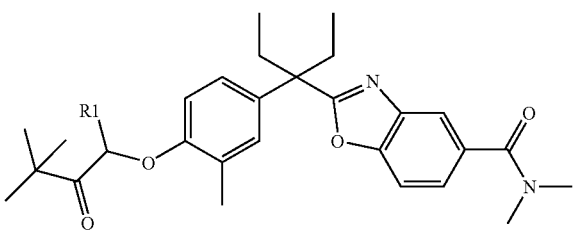

C13)

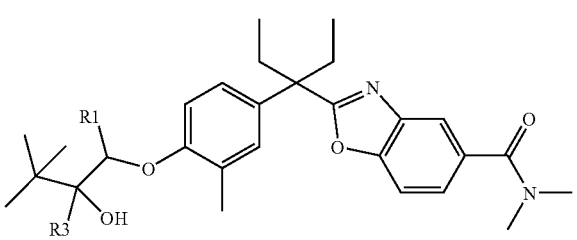

C14)

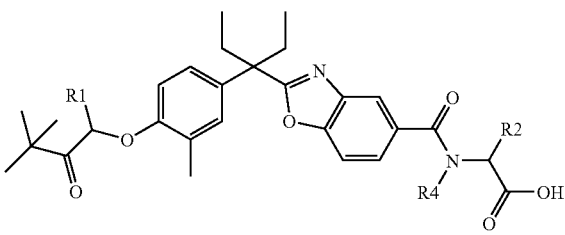

C15)

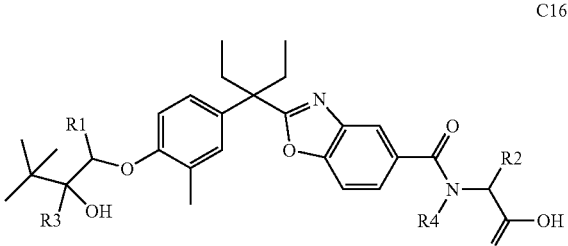

C16)

where R1 is H, Me, or Et; R2 is H or Me; R3 is H, Me or Et; and R4 is H or Me. Particularly preferred compounds include compounds representated by formulae $C_1$-$C_{16}$ where R1 is Me or Et; and R2, R3, R4 individually are H or Me.

EXAMPLES

General Experimental Conditions:

The starting material/intermediate is the compound from the immediate preceding experimental unless otherwise indicated.

All reactions are performed under nitrogen/argon atmosphere, in a stirred reaction vessel, and at room temperature unless indicated otherwise.

Unless otherwise indicated, the notation that "organic layer is $MgSO_4$/$Na_2SO_4$ dried" "dryed over $MgSO_4$/$Na_2SO_4$" is defined as swirling or stirring the solution with a dessicant ($MgSO_4$ and/or $Na_2SO_4$) 5-15 m, then filtering off the dessicant to give an anhydrous filtrate.

For analogous multi-step reaction procedures, the yield is given either for the ultimate step or overall multi-steps as indicated.

Solutions are "concentrated" at a range of 25-75° C. with reduced pressure (0.05 to 1 mm).

Unless otherwise indicated, "the residue is chromatographed" is defined as silica gel chromatography of residue with moderate nitrogen pressure (flash chromatography) or a medium pressure chromatography systems using a silica gel to crude product ratio of ~10-100.

For HPLC, the conditions listed are for the analytical trace only. For Preparative HPLC, the eluent is similar to analytical HPLC eluent.

Thin layer chromatography is performed with silica gel plates with UV and/or appropriate staining solution.

NMR spectra are obtained with either 300 or 400 mHz spectrometer.

NMR data is listed to denote spectrum is consistent with assigned structure.

"NMR" notation without data denotes spectrum is consistent with assigned structure.

HRMS—high resolution mass spectrum
ES-MS—electrospray mass spectrum
Abbreviations:
Aq—aqueous
d—day
eq—equivalent
h—hour
m—minute
satd—saturated
disp—dispersion
quant—quantitative
rt for retention time (both small caps to minimize confusion with RT)

RT—room temperature

TABLE 1

Chemical Terms

| Term | Definition | Term | Definition |
|---|---|---|---|
| BF3-OEt2 | boron trifluoride etherate | MeOH | methanol |
| BnBr | benzyl bromide | NMO | 4-methylmorpholine N-oxide |
| CH2Cl2 | Dichloromethane | NMP | N-methylpyrrolidin-2-one |
| DMAP | 4-(dimethylamino)pyridine | Na—S—R3 | sodium alkylmercaptide |
| DMF | N,N-dimethylformamide | PBr3 | phosphorus tribromide |
| DMSO | Dimethylsulfoxide | Pd(DPPF) | palladium dichloro[1,1'-bis(diphenylphosphino) ferrocene |
| DPPB | 1,4-bis(diphenylphosphino) butane | Pd(OAc)2 | palladium (II) acetate |
| DPPF | dichloro[1,1'-bis(diphenylphosphino) ferrocene | Pd(TPP)4 | palladium tetrakistriphenylphosphine |
| EDCI | 3-Ethyl-1-[3-(dimethylamino) propyl]carbodiimide hydrochloride | Pd—C | palladium on carbon |
| EEDC | Diethyl cyanamide | Pd—C/H2 | palladium on carbon with hydrogen pressure |
| EtMgBr | ethyl magnesium bromide | pTSA | para-toluenesulfonic acid |
| EtOAc | ethyl acetate | Pyr | pyridine |
| EtOH | Ethanol | Red-Al | sodium bis(2-methoxyethoxy)aluminum hydride |
| H2 | hydrogen pressure | R2MgBr | alkyl magnesium bromide |
| H2NCH2CO2Me | methyl glycinate | R3MgBr | alkyl magnesium bromide |
| Hept | Heptane | R5MgBr | alkyl magnesium bromide |
| Hex | Hexanes | R3S(O)2Cl | alkylsulfonyl chloride |
| HN(OMe)Me | N-methyl-O-methyl hydroxylamine | R2S(O)2NH2 | alkylsulfonamide |
| HNMe2 | dimethyl amine | TBSCl | tert-butyldimethylsilyl chloride |
| HATU | O-(7-azabenzotriazol-1-yl)-N,N,N',N'-tetramethyl uronium hexafluorophosphate | tBuC(O)CH2Br— | 1-bromopinacolone |
| HOAT | 7-aza-1-hydroxy benzotriazole | Tf2O | triflic anhydride |
| HOBT | 1-hydroxybenzotriazole | TFA | trifluoroacetic acid |
| K2CO3 | potassium carbonate | THF | tetrahydrofuran |
| LAH | lithium aluminum hydride | Ti(OiPr)4 | titanium tetraisopropoxide |
| LiHMDS | lithium hexamethyl disilazide | TMS-acetylene | trimethylsilyl acetylene |
| Lindlar catalyst | Pd—CaCO$_3$—PbO | TPAP | tetrapropylammonium perruthenate |
| mCPBA | meta-chloroperbenzoic acid | Zn(OTf)2 | zinc trifluoro methane sulfonate |
| TPA | 12-O-tetradecanoyl 13-acetate (Sigma) | PHA | Phytohemagglutinin (Sigma) |
| TEA | Triethylamine | NMM | N methylmorpholine |

General Procedures
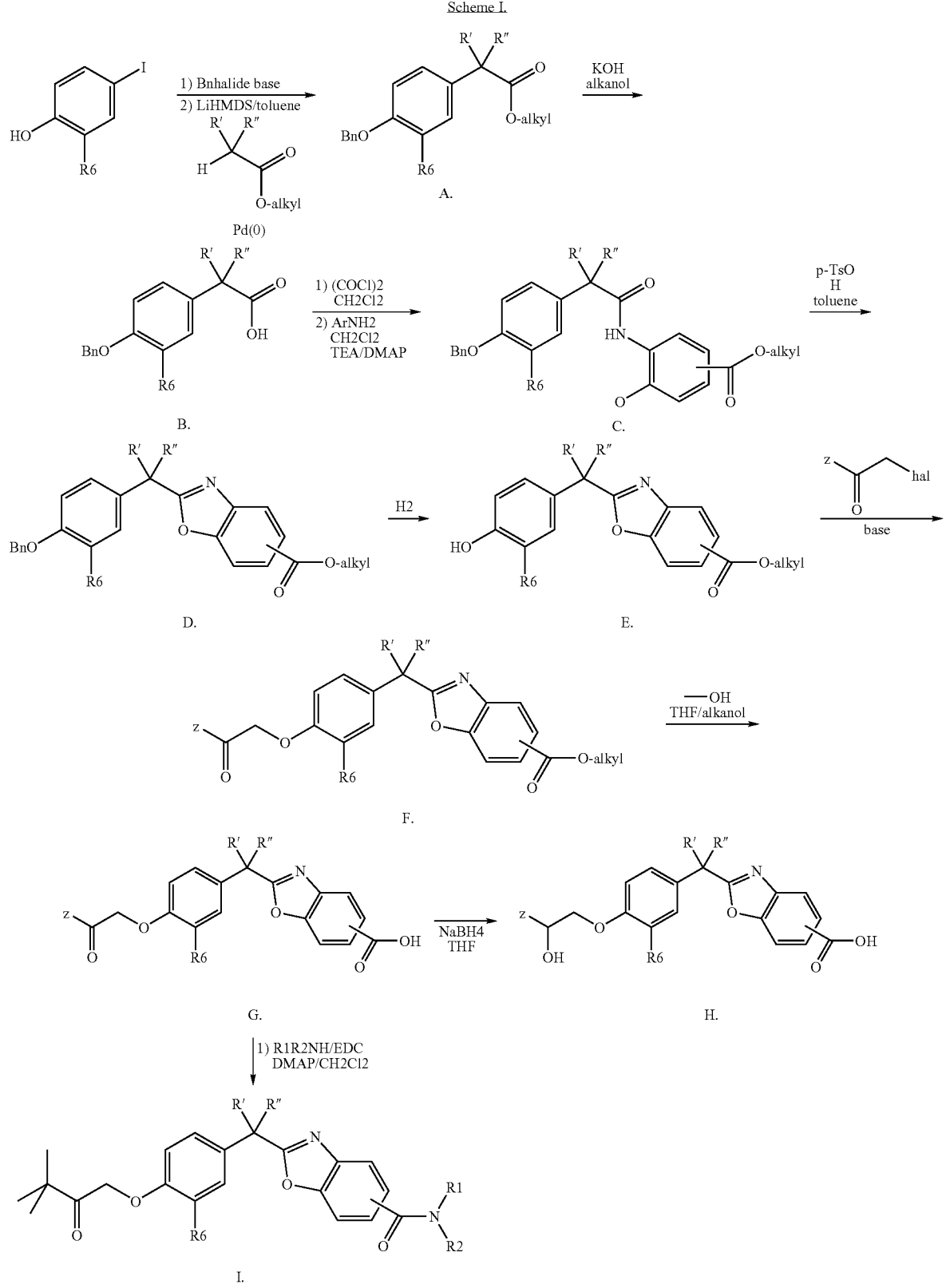

Scheme I.

A 2-substituted-4-iodophenol is protected with a benzyl halide in base, such as, potassium carbonate in a polar aprotic solvent, e.g., acetone or acetonitrile from room temperature to the reflux temperature of the reaction mixture to give the benzyl protected phenol intermediate. This is coupled in the presence of a palladium catalyst to the alpha-anion of an alpha-alkyl alkanoate using LiHMDS from 100 to 160° C. to give the ester A. The ester A is saponified with lithium, potassium, or sodium hydroxide in an alkanol from room temperature to the reflux temperature of the mixture to give the acid B. Acid B is converted to the acid halide, e.g., with phosgene or phosgene/DMF and reacted with a substituted o-hydroxyaniline in the presence of base, e.g., TEA to give the carboxanilide C. The carboxanilide C is dehydrated, e.g., with acid/toluene at the reflux temperature of the mixture to give the benzoxazole D. Benzyl protection is removed from benzoxazole D by hydrogenation with a palladium catalyst, e.g., Pd—C to give the benzoxazole E. The free hydroxyl of the benzoxazole E. is alkylated with an alpha-halo ketone (z-C(O)CH$_2$hal, where z is an alkyl group or a substituted alkyl group) in base, e.g., potassium carbonate in a polar aprotic solvent such as, acetone or acetonitrile from room temperature to the reflux temperature of the mixture to give the alkylated benzoxazole F. Saponification of the benzoxazole F with lithium, potassium, or sodium hydroxide in an alkanol from room temperature to the reflux temperature of the mixture gives the acid G. Acid G is reduced with lithium or sodium borohydride or cyanoborohydride in an alkanol or THF to give the carbinol H. Both acids G and H, as is well known in the art, are coupled to primary or secondary amines using, e.g., EDC to produce carboxamides such as I or the carbinol derivative of I.

Scheme II.

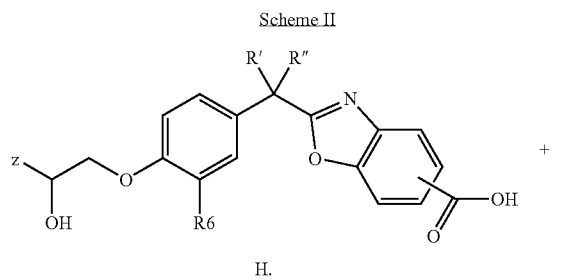

H.

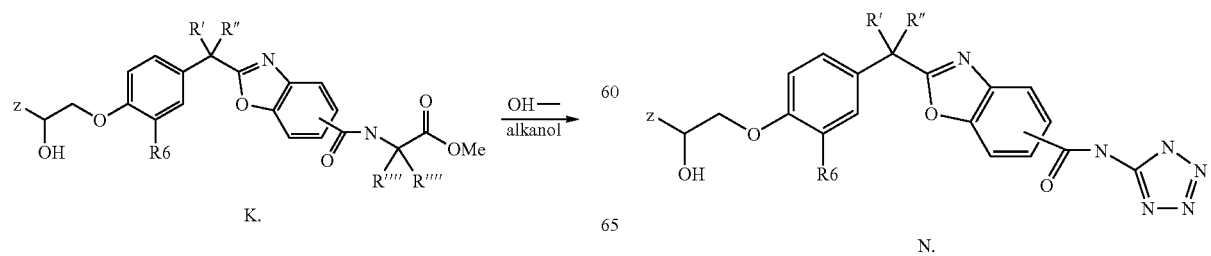

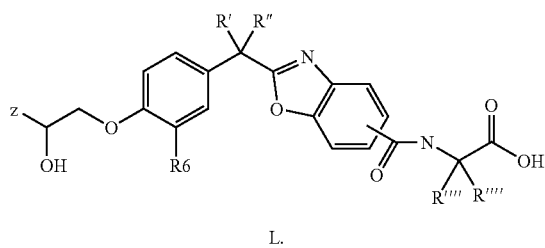

L.

R'''' = H, Me, Et or
R'''' and R''''' together from a C3-C6 ring

Scheme II.

Carbinol H is coupled with amino acid ester J, using common coupling agents, such as, EDCI, HOBT, and N-methylmorpholine to give amide ester K. Coupling of carbinol H with a cyclic amino acid ester J (R'''' and R''''' to form ring) gives the corresponding cyclic amide-ester K. Amide ester K is treated with an alkali hydroxide and an alkanol to give amide acid L.

Scheme III

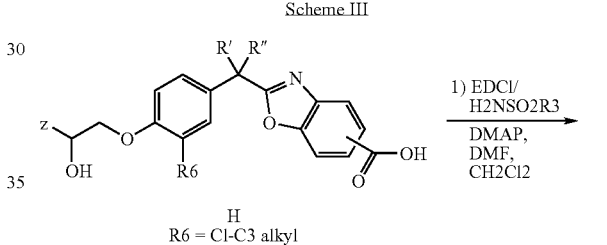

H
R6 = Cl-C3 alkyl

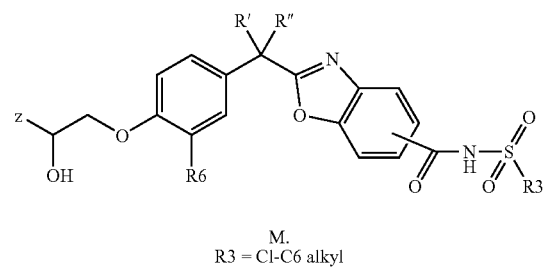

M.
R3 = Cl-C6 alkyl

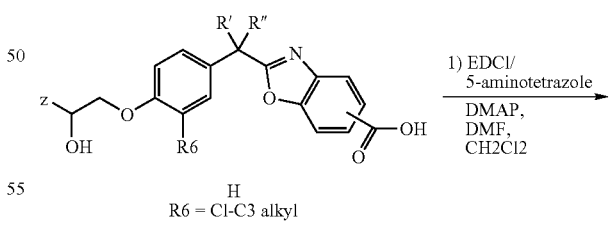

H
R6 = Cl-C3 alkyl

N.

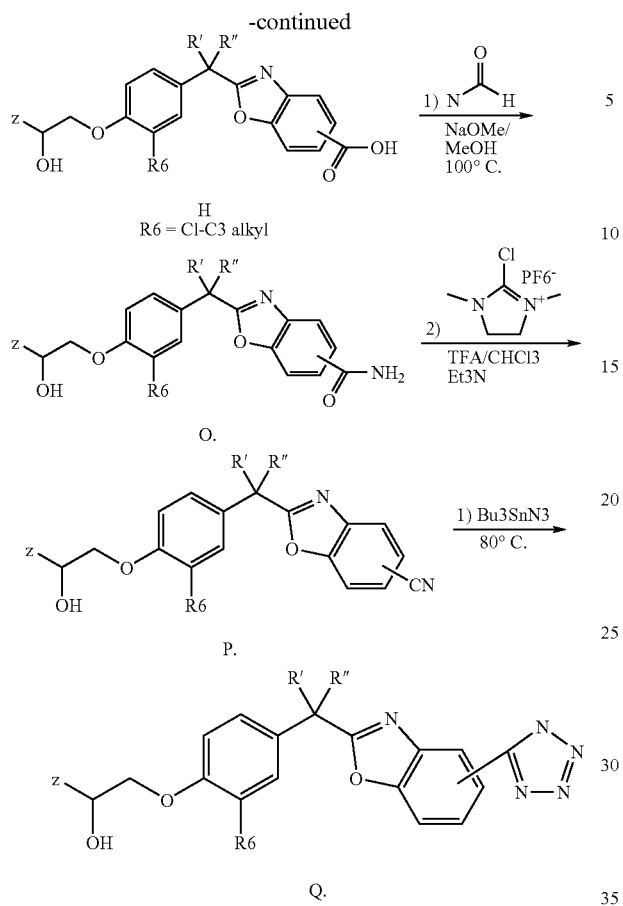

Scheme III.

Carbinol H is coupled with alkylsulfonamide, EDCI, and DMAP to give acylsulfonamide M. Carbinol H is coupled with 5-aminotetrazole, EDCI, and DMAP to give acylaminotetrazole N. Carbinol H is reacted with formamide and NaOMe at 100° C. to produce amide O. Amide O is reacted with Et3N, 2-chloro-1,3-dimethylimidazolinium hexafluorophosphate, and TFA to afford nitrile P. Nitrile P is reacted with Bu3SnN3 at 80° C. to give tetrazole Q.

EXAMPLES

Example 1

Preparation of 2-{1-[4-(3,3-dimethyl-2-oxo-butoxy)-3-methyl-phenyl]-1-ethyl-propyl}-benzooxazole-6-carboxylic acid

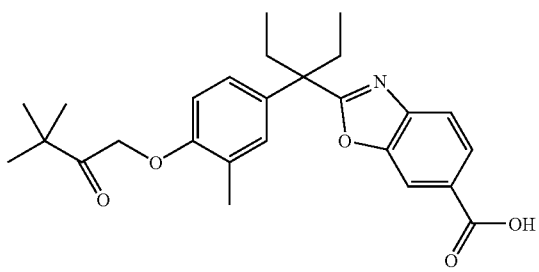

A. 1-Benzyloxy-4-iodo-2-methyl-benzene

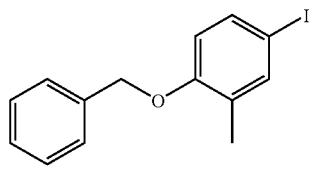

A mechanically stirred mixture of 4-iodo-2-methylphenol (1.62 moles; 391 g), cesium carbonate (1.99 moles; 650 g), and 1.75 L of acetone is treated with benzyl bromide (1.70 moles; 203 mL; 291 g) over 15 m. The reaction mixture was stirred for 21 h at RT and filtered. The filter cake is washed with 1 L of acetone, and the combined filtrates are concentrated. The crude semi-solid is recrystallized from pentane to give 475 grams (90%) of the desired product as a white solid. $^1$H NMR (CDCl$_3$) δ: 7.40 (m, 7H), 6.64 (d, J=8.6 Hz, 1H), 5.06 (s, 2H), 2.24 (s, 3H).

B. 2-(4-Benzyloxy-3-methyl-phenyl)-2-ethyl-butyric acid methyl ester

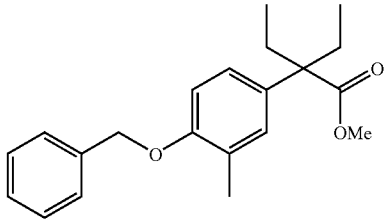

To a mixture of 1-benzyloxy-4-iodo-2-methyl-benzene (494 mmoles; 160 g) and lithium bis(trimethylsilyl)amide (1.20 moles; 200 g) in 250 ml of toluene at 0-5° C. is added a solution of 2-ethyl-butyric acid methyl ester (988 mmoles; 129 g, Synthesis, 1985 (3), 320) in 250 ml of toluene over 30 m, causing the reaction to exotherm to 18 C. The cloudy yellow solution is allowed to warm to RT and stir for 20 m. Tri-tert-butylphosphine (4.94 mmoles; 1.30 mL; 1.00 g) in 200 ml of toluene and bis(dibenzylideneacetone)palladium (7.90 mmoles; 4.54 g) are added sequentially, and the dark mixture is stirred at ambient temperature for 62 h. The mixture is diluted with 1 L of EtOAc, filtered through a bed of Hyflo, and rinsed with another 1 L of EtOAc. The filtrate is concentrated. The dark orange oil (~200 g) is purified by flash chromatography (10% EtOAc/hexanes, 1 kg of silica) to give the title compound as a light orange oil (72.4 g). The mixed fractions are combined and re-subjected to the same chromatography conditions to give the another batch of title compound as a yellow oil (50.6 g). $^1$H NMR (CDCl$_3$) δ 7.40 (m, 5H), 7.02 (m, 2H), 6.83 (d, J=9.2 Hz, 1H), 5.06 (s, 3H), 3.64 (s, 3H), 2.27 (s, 3H), 2.02 (m, 4H), 0.73 (t, J=7.4 Hz, 6H).

C. 2-(4-Benzyloxy-3-methyl-phenyl)-2-ethyl-butyric acid

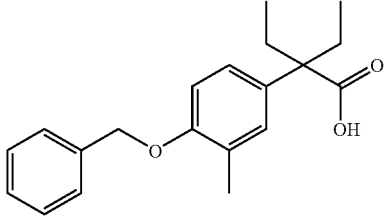

To a mixture of 2-(4-benzyloxy-3-methyl-phenyl)-2-ethyl-butyric acid (265 mmoles; 86.4 g), 860 ml of 95% ethanol, and 300 ml of water is added potassium hydroxide (2.05 moles; 115 g). The cloudy yellow solution is heated at 70° C. overnight. The mixture is concentrated, and the residue is partitioned between 1.5 L of MTBE and 1.5 L of 1N HCl. The organic layer is washed with 1 L of 1N HCl, dried over MgSO4, and concentrated. The crude product (~80 g) was slurried in hexanes (350 ml). After stirring for 1 h, the solid was filtered, washed with hexanes, and dried in vacuo at 35° C. to give 57.2 g (69%) of the title compound as a white solid. $^1$H NMR (CDCl$_3$) δ 7.38 (m, 5H), 7.09 (m, 2H), 6.84 (d, J=9.2 Hz, 1H), 5.06 (s, 2H), 2.28 (s, 3H), 2.04 (m, 4H), 0.77 (t, J=7.4 Hz, 6H).

D. 4-[2-(4-Benzyloxy-3-methyl-phenyl)-2-ethyl-butyrylamino]-3-hydroxy-benzoic acid methyl ester

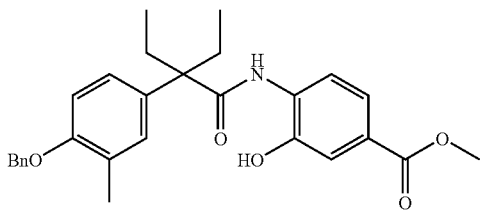

A solution of 2-(4-benzyloxy-3-methyl-phenyl)-2-ethyl-butyryl acid (5.20 g, 16.6 mmol) in CH$_2$Cl$_2$ (50 mL) at 0° C. is treated with (COCl)$_2$ (6.34 g, 49.9 mmol), followed by addition of DMF (0.2 mL). The reaction mixture is stirred for 10 m and the cooling bath is removed. The mixture is continued to stir for 2 h at RT and concentrated to intermediate 2-(4-benzyloxy-3-methyl-phenyl)-2-ethyl-butyryl chloride (5.40 g, 98%).

The solution of the acid chloride (5.40 g, 16.3 mmol) in CH$_2$Cl$_2$ (100 mL) is added 4-amino-3-hydroxy-benzoic acid methyl ester (3.27 g, 19.6 mmol). The mixture is added TEA (6.90 ml, 48.9 mmol) and DMAP (100 mg, 0.82 mmol) and stirred at RT for 2 h. The reaction is quenched with water (100 mL) and the aqueous layer is extracted with EtOAc (2×50 mL). The combined organic layers are dried over Na$_2$SO$_4$, concentrated, purified on column chromatography (25% EtOAc/Hex) to afford the title compound (5.30 g, 70%). MS (ES) m/e: 462.3 (M+1), 460.2 (M−1)

E. 2-[1-(4-Benzyloxy-3-methyl-phenyl)-1-ethyl-propyl]-benzooxazole-6-carboxylic acid methyl ester

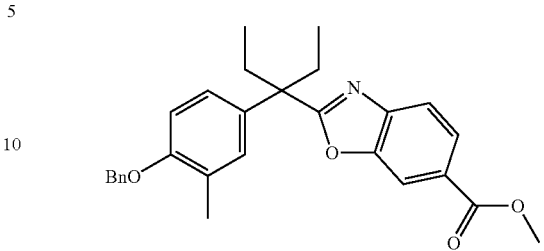

A solution of 4-[2-(4-benzyloxy-3-methyl-phenyl)-2-ethyl-butyrylamino]-3-hydroxy-benzoic acid methyl ester (2.15 g, 4.66 mmol) in toluene (50 mL) is treated with TsOH—H$_2$O (443 mg, 2.33 mmol). The reaction is heated to 160° C. for 60 m. The reaction mixture is cooled down, and toluene is removed under vacuum. The residue is purified by column chromatography (10% EtOAc/Hex) to give the title compound as an oil (1.50 g, 72%) MS (ES) m/e: 444.2 (M+1).

F. 2-[1-Ethyl-1-(4-hydroxy-3-methyl-phenyl)-propyl]-benzooxazole-6-carboxylic acid methyl ester

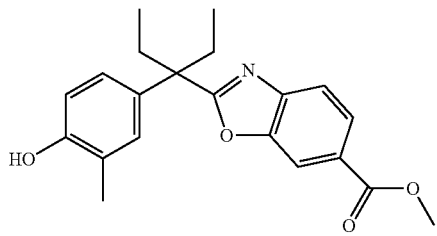

A solution of 2-[1-(4-benzyloxy-3-methyl-phenyl)-1-ethyl-propyl]-benzooxazole-6-carboxylic acid methyl ester (1.50 g, 3.38 mmol) in MeOH (20 mL) is added a slurry of Pd—C (150 mg, 10%) in THF (20 mL) at RT. The resulting mixture is stirred under hydrogen balloon pressure for 12 h. The mixture is filtered through a pad of celite, and the filtrate is concentrated. The residue is purified with 20% EtOAc/Hex to afford the title compound (1.20 g, 100%). H-NMR (ppm, CDCl$_3$) δ: 8.11 (1H, s), 8.03 (1H, dd, J=1.8, 8.4 Hz), 7.73 (1H, d, J=8.4 Hz), 6.97 (1H, d, J=2.2 Hz), 6.92 (1H, dd, J=2.2, 8.4 Hz), 6.70 (1H, d, J=8.4 Hz), 3.93 (3H, s), 2.40 (2H, q, J=7.5 Hz), 2.30 (2H, q, J=7.5 Hz), 2.20 (3H, s), 0.76 (6H, t, J=7.5 Hz).

G. 2-{1-[4-(3,3-Dimethyl-2-oxo-butoxy)-3-methyl-phenyl]-1-ethyl-propyl}-benzooxazole-6-carboxylic acid methyl ester

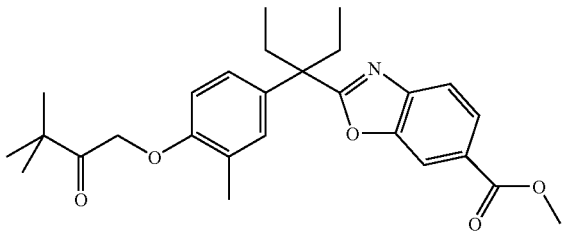

2-[1-Ethyl-1-(4-hydroxy-3-methyl-phenyl)-propyl]-benzooxazole-6-carboxylic acid methyl ester (1.20 g, 3.38 mmol) in acetone (40 mL) is treated with 1-bromopinacolone (0.73 g, 4.06 mmol) and K$_2$CO$_3$ (0.93 g, 6.76 mmol). The suspension is stirred at RT for 4 h. The mixture is filtered, and the filtrate is concentrated. The residue is purified using silica gel column chromatography (15% EtOAc/Hex) to give the title compound as a pale yellow oil (1.50 g, 98%). H-NMR (ppm, CDCl$_3$) δ: 8.14 (1H, d, J=2.4 Hz), 8.07 (1H, dd, J=1.2, 8.4 Hz), 7.78 (1H, d, J=8.4 Hz), 7.05 (1H, d, J=1.6 Hz), 7.00 (1H, dd, J=2.4, 8.4 Hz), 6.56 (1H, d, J=8.4 Hz), 4.87 (2H, s), 3.96 (3H, s), 2.40 (2H, q, J=7.5 Hz), 2.30 (2. H, q, J=7.5 Hz), 2.28 (3H, s), 1.27 (9H, s), 0.77 (6H, t, J=7.5 Hz).

H. 2-{1-[4-(3,3-Dimethyl-2-oxo-butoxy)-3-methyl-phenyl]-1-ethyl-propyl}-benzooxazole-6-carboxylic acid

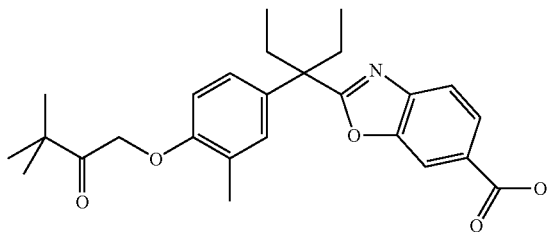

2-{1-[4-(3,3-Dimethyl-2-oxo-butoxy)-3-methyl-phenyl]-1-ethyl-propyl}-benzooxazole-6-carboxylic acid methyl ester (1.50 g, 3.32 mmol) in MeOH (10 mL) and THF (10 mL) is treated with NaOH (2.0 M, 20.0 mL). The resulting mixture is stirred at RT for 16 h. The mixture is concentrated, acidified with HCl (5 N) until pH~3, and extracted with EtOAc (100 mL, then 50 mL). The organic layer is dried over Na$_2$SO$_4$, filtered, and concentrated to afford the title compound (1.40 g, 97%). H-NMR (ppm, CDCl$_3$) δ: 8.16 (1H, d, J=1.3 Hz), 8.11 (1H, dd, J=1.3, 8.4 Hz), 7.78 (1H, d, J=8.4 Hz), 7.02 (1H, d, J=1.8 Hz), 6.97 (1H, dd, J=2.2, 8.4 Hz), 6.54 (1H, d, J=8.4 Hz), 4.85 (2H, s), 2.40 (2H, q, J=7.5 Hz), 2.30 (2H, q, J=7.5 Hz), 2.26 (3H, s), 1.25 (9H, s), 0.77 (6H, t, J=7.5 Hz). MS (ES) m/e: 438.2 (M+1), 436.2 (M−1).

Example 2

Preparation of 2-{1-[4-(3,3-Dimethyl-2-oxo-butoxy)-3-methyl-phenyl]-1-ethyl-propyl}-benzooxazole-6-carboxylic acid amide

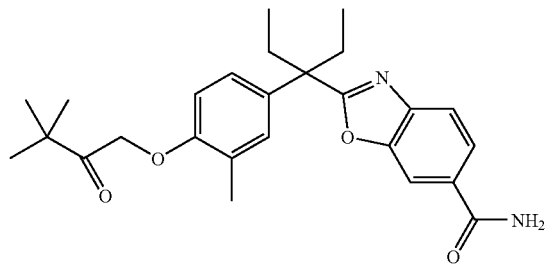

A solution of 2-{1-[4-(3,3-dimethyl-2-oxo-butoxy)-3-methyl-phenyl]-1-ethyl-propyl)}-benzooxazole-6-carboxylic acid (150 mg, 0.343 mmol) in CH$_2$Cl$_2$ (5.0 mL) is treated with DMAP (125 mg, 1.03 mmol) and EDC (99 mg, 0.514 mmol). The mixture is stirred for 15 m at RT before the addition of aqueous ammonium hydroxide (1.0 mL, 30%). The reaction is stirred for 18 h and quenched with aqueous NH$_4$Cl (5.0 mL). The organic layer is loaded on silica gel column and purified with 50% EtOAc/Hex to afford the title compound (40 mg, 27%). MS (ES) m/e: 437.3 (M+1).

Example 3

Preparation of 2-{1-[4-(3,3-Dimethyl-2-oxo-butoxy)-3-methyl-phenyl]-1-ethyl-propyl}-benzooxazole-6-carboxylic acid dimethylamide

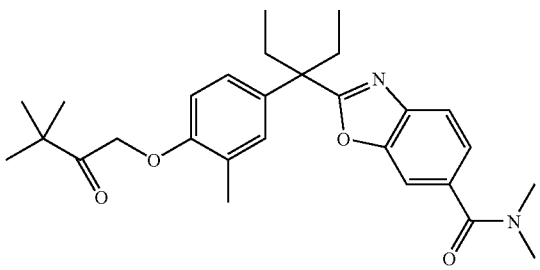

2-{1-[4-(3,3-Dimethyl-2-oxo-butoxy)-3-methyl-phenyl]-1-ethyl-propyl}-benzooxazole-6-carboxylic acid (150 mg, 0.343 mmol) in CH$_2$Cl$_2$ (5.0 mL) is treated with DMAP (125 mg, 1.03 mmol) and EDC (99 mg, 0.514 mmol). The mixture is stirred for 15 m at RT, and dimethylamine hydrochloride (42 mg, 0.514 mmol) is added. The reaction is stirred for 18 h and quenched with aqueous NH$_4$Cl (5.0 mL). The organic layer is loaded onto a silica gel column and purified with 50% EtOAc/Hex to afford the title compound (125 mg, 79%). MS (ES) m/e: 465.3 (M+1).

Example 4

Preparation of [(2-{1-[4-(3,3-dimethyl-2-oxo-butoxy)-3-methyl-phenyl]-1-ethyl-propyl}-benzooxazole-6-carbonyl)-amino]-acetic acid

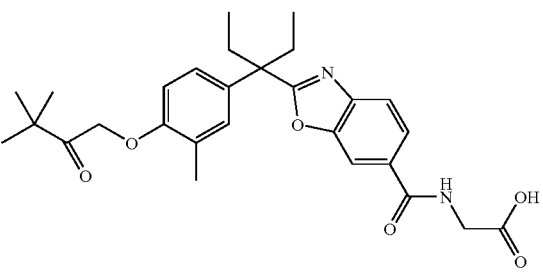

2-{1-[4-(3,3-Dimethyl-2-oxo-butoxy)-3-methyl-phenyl]-1-ethyl-propyl}-benzooxazole-6-carboxylic acid (150 mg, 0.343 mmol) in CH$_2$Cl$_2$ (5.0 mL) is treated with DMAP (125 mg, 1.03 mmol) and EDC (99 mg, 0.514 mmol). The mixture is stirred for 15 m at RT, and glycine methyl ester hydrochloride (64 mg, 0.514 mmol) is added. The reaction is stirred for 18 h and quenched with NH$_4$Cl (5.0 mL). The organic layer is loaded onto a silica gel column and purified with 20-50% EtOAc/Hex to afford the intermediate amide ester.

The intermediate is dissolved in methanol (2.0 µl) and THF (2.0 mL) and treated with NaOH (2.0 M, 5.0 mL). The resulting mixture is stirred at RT for 3 h. The mixture is concentrated, acidified with HCl (1 N) to pH~3, and extracted with EtOAc (2×20 mL). The organic layer is dried over Na$_2$SO$_4$ and concentrated to afford the title compound (95 mg, 56%). MS (ES) m/e: 495.2 (M+1), 493.3 (M−1).

Example 5

Preparation of 2-{1-[4-(3,3-Dimethyl-2-oxo-butoxy)-3-methyl-phenyl]-1-ethyl-propyl}-benzooxazole-5-carboxylic acid

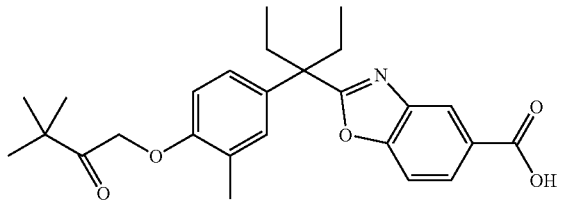

A. 3-[2-(4-Benzyloxy-3-methyl-phenyl)-2-ethyl-butyrylamino]-4-hydroxy-benzoic acid methyl ester

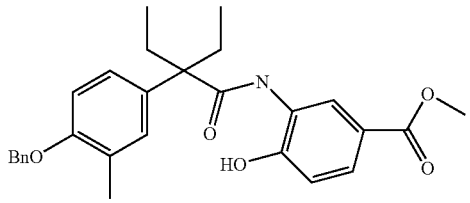

A solution of 2-(4-benzyloxy-3-methyl-phenyl)-2-ethyl-butyryl acid (4.60 g, 14.7 mmol) in CH$_2$Cl$_2$ (100 mL) at 0° C. is treated with (COCl)$_2$ (6.73 g, 35.3 mmol), followed by addition of DMF (0.2 mL). The reaction mixture is stirred for 10 m and the cooling bath is removed. The mixture is continued to stir for 2 h at RT and concentrated to 2-(4-benzyloxy-3-methyl-phenyl)-2-ethyl-butyryl chloride (5.40 g, 98%).

The solution of the acid chloride (5.40 g, 16.3 mmol) in CH$_2$Cl$_2$ (100 mL) is added 3-amino-4-hydroxy-benzoic acid methyl ester (2.95 g, 17.7 mmol). The mixture is added TEA (6.18 ml, 44.1 mmol) and DMAP (100 mg, 0.82 mmol) and stirred at RT for 2 h. The reaction is quenched with water (100 mL) and the aqueous layer is extracted with EtOAc (2×50 mL). The combined organic layers are dried over Na$_2$SO$_4$, concentrated, purified on column chromatography (25% EtOAc/Hex) to afford the title compound (5.80 g, 86%). MS (ES) m/e: 462.3 (M+1), 460.2 (M−1)

B. 2-[1-(4-Benzyloxy-3-methyl-phenyl)-1-ethyl-propyl]-benzooxazole-5-carboxylic acid methyl ester

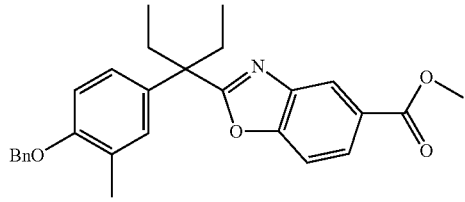

3-[2-(4-Benzyloxy-3-methyl-phenyl)-2-ethyl-butyrylamino]-4-hydroxy-benzoic acid methyl ester (5.80 g, 12.6 mmol), TsOH—H$_2$O (478 mg, 2.51 mmol) in toluene (100 mL) are reacted analogous to Example 1, step E to give the title product (5.08 g, 91%). MS (ES) m/e: 444.2 (M+1).

C. 2-[1-Ethyl-1-(4-hydroxy-3-methyl-phenyl)-propyl]-benzooxazole-5-carboxylic acid methyl ester (PF1-A05244-036A)

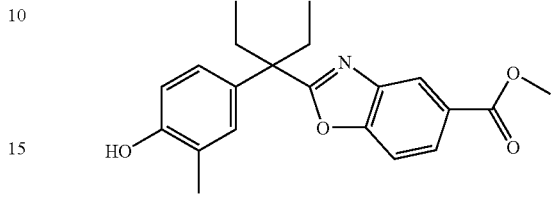

2-[1-(4-Benzyloxy-3-methyl-phenyl)-1-ethyl-propyl]-benzooxazole-5-carboxylic acid methyl ester (3.28 g, 7.39 mmol) and Pd—C (300 mg, 10%) is hydrogenated analogous to Example 1, step F to give the title product (2.10 g, 80%). MS (ES) m/e: 354.2 (M+1), 352.2 (M−1).

D. 2-{1-[4-(3,3-Dimethyl-2-oxo-butoxy)-3-methyl-phenyl]-1-ethyl-propyl}-benzooxazole-5-carboxylic acid methyl ester

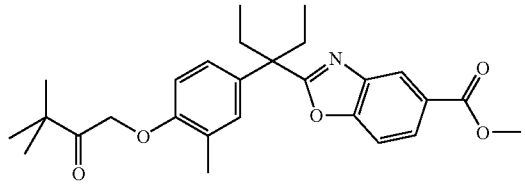

2-[1-Ethyl-1-(4-hydroxy-3-methyl-phenyl)-propyl]-benzooxazole-5-carboxylic acid methyl ester (2.10 g, 5.94 mmol) and 1-bromopinacolone (1.59 g, 8.87 mmol) and K$_2$CO$_3$ (2.04 g, 14.8 mmol) are reacted analogous to Example 1, step G to give the title compound as a pale yellow oil (2.55 g, 95%). H-NMR (ppm, CDCl$_3$) δ: 8.43 (1H, d, J=1.3 Hz), 8.01 (1H, dd, J=1.8, 8.8 Hz), 7.42 (1H, d, J=8.4 Hz), 7.01 (1H, d, J=2.2 Hz), 6.96 (1H, dd, J=2.2, 8.4 Hz), 6.51 (1H, d, J=8.8 Hz), 4.84 (2H, s), 3.95 (3H, s), 2.38 (2H, q, J=7.5 Hz), 2.32 (2H, q, J=7.5 Hz), 2.25 (3H, s), 1.25 (9H, s), 0.76 (6H, t, J=7.5 Hz).

E. 2-{1-[4-(3,3-Dimethyl-2-oxo-butoxy)-3-methyl-phenyl]-1-ethyl-propyl}-benzooxazole-5-carboxylic acid

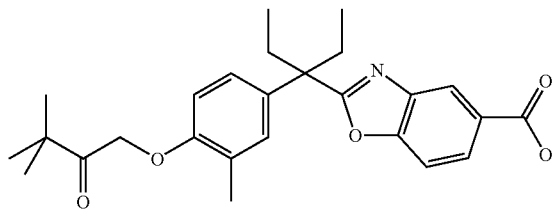

2-{1-[4-(3,3-Dimethyl-2-oxo-butoxy)-3-methyl-phenyl]-1-ethyl-propyl}-benzooxazole-5-carboxylic acid methyl ester (2.55 g, 5.65 mmol) is hydrolyzed analogous to Example 1, step H to give the title compound as a pale yellow oil (2.46 g, 99%). H-NMR (ppm, CDCl$_3$) δ: 8.51 (1H, d, J=1.8 Hz), 8.08 (1H, dd, J=1.8, 8.4 Hz), 7.45 (1H, d, J=8.8 Hz), 7.02 (1H, d, J=2.2 Hz), 6.96 (1H, dd, J=2.2, 8.4 Hz), 6.52 (1H, d, J=8.8 Hz), 4.84 (2H, s), 2.38 (2H, q, J=7.5 Hz), 2.32 (2H, q, J=7.5 Hz), 2.26 (3H, s), 1.25 (9H, s), 0.76 (6H, t, J=7.5 Hz). MS (ES) m/e: 438.2 (M+1), 436.2 (M−1).

Example 6

Preparation of 2-{1-Ethyl-1-[4-(2-hydroxy-3,3-dimethyl-butoxy)-3-methyl-phenyl]-propyl}-benzooxazole-5-carboxylic acid

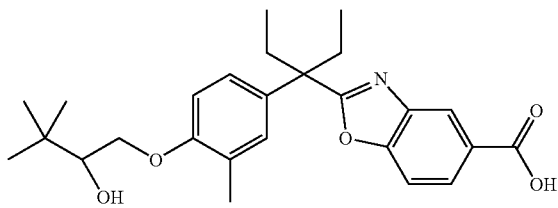

2-{1-[4-(3,3-Dimethyl-2-oxo-butoxy)-3-methyl-phenyl]-1-ethyl-propyl}-benzooxazole-5-carboxylic acid (0.58 g, 1.33 mmol) in THF (30 mL) at RT is treated with NaBH$_4$ (100 mg, 2.65 mmol). The resulting mixture is stirred for 1 h. The reaction is quenched with HCl (1.0 N, 5.0 mL) and extracted with EtOAc (3×50 mL). The organic layer is dried over Na$_2$SO$_4$ and concentrated to afford the title compound (0.58 g, 100%). MS (ES) m/e: 440.3 (M+1), 438.2 (M−1).

Example 7

Preparation of 2-{1-[4-(3,3-Dimethyl-2-oxo-butoxy)-3-methyl-phenyl]-1-ethyl-propyl}-benzooxazole-5-carboxylic acid amide

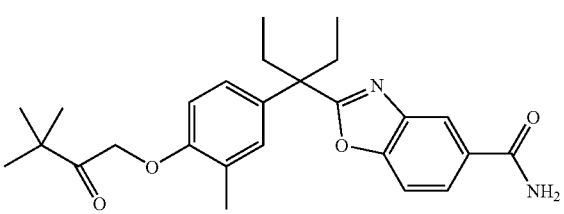

2-{1-[4-(3,3-Dimethyl-2-oxo-butoxy)-3-methyl-phenyl]-1-ethyl-propyl}-benzooxazole-5-carboxylic acid (150 mg, 0.343 mmol), DMAP (125 mg, 1.03 mmol) and EDC (99 mg, 0.514 mmol) and aqueous ammonium hydrroxide (1.0 mL, 30%) is reacted analogous to Example 2 to give the title product (10 mg, 7%). MS (ES) m/e: 437.3 (M+1).

Example 8

Preparation of 2-{1-[4-(3,3-Dimethyl-2-oxo-butoxy)-3-methyl-phenyl]-1-ethyl-propyl}-benzooxazole-5-carboxylic acid dimethylamide

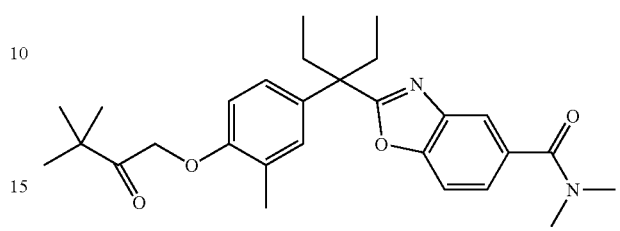

2-{1-[4-(3,3-Dimethyl-2-oxo-butoxy)-3-methyl-phenyl]-1-ethyl-propyl}-benzooxazole-5-carboxylic acid (150 mg, 0.343 mmol), DMAP (125 mg, 1.03 mmol), EDC (99 mg, 0.514 mmol), and dimethylamine hydrochloride (42 mg, 0.514 mmol) are reacted analogous to Example 3 to give the title product (80 mg, 50%). MS (ES) m/e: 465.3 (M+1).

Example 9

Preparation of [(2-{1-[4-(3,3-Dimethyl-2-oxo-butoxy)-3-methyl-phenyl]-1-ethyl-propyl}-benzooxazole-5-carbonyl)-amino]-acetic acid

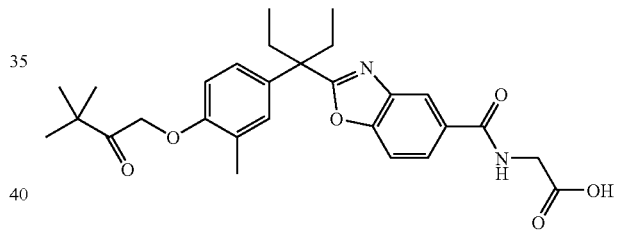

2-{1-[4-(3,3-Dimethyl-2-oxo-butoxy)-3-methyl-phenyl]-1-ethyl-propyl}-benzooxazole-5-carboxylic acid (150 mg, 0.343 mmol), DMAP (125 mg, 1.03 mmol), EDC (99 mg, 0.514 mmol), and glycine methyl ester hydrochloride (64 mg, 0.514 mmol) are reacted and hydrolyzed analogous to Example 4 to give the title product (130 mg, 76%). MS (ES) m/e: 495.3 (M+1), 493.3 (M−1).

Compounds of the Invention—Salts, Stereoisomers, & Prodrugs:

Salts of the compounds represented by Formula I are an additional aspect of the invention. The skilled artisan will also appreciate that the family of compounds of Formula I include acidic and basic members and that the present invention includes pharmaceutically acceptable salts thereof.

In those instances where the compounds of the invention possess acidic or basic functional groups various salts may be formed which are more water soluble and physiologically suitable than the parent compound. Representative pharmaceutically acceptable salts, include but are not limited to, the alkali and alkaline earth salts such as lithium, sodium, potassium, ammonium, calcium, magnesium, aluminum, zinc, and the like. Sodium and potassium salts are particularly preferred. Salts are conveniently prepared from the free acid by treating the acid in solution with a base or by exposing the acid to an ion exchange resin. For example, a carboxylic acid substituent on the compound of Formula I may be selected as —CO$_2$H and salts may be formed by reaction with appropriate bases (e.g., NaOH, KOH) to yield the corresponding sodium and potassium salt.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1-19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, bromide, camsylate, carbonate, chloride, choline, clavulanate, citrate, chloride, chloroprocaine, choline, diethanolamine, dihydrochloride, diphosphate, edetate, edisylate, estolate, esylate, ethylenediamine, fluoride, fumarate, gluceptate, gluconate, glutamate, glycolylarsanilate, hexylresorcinate, hydrabamine, bromide, chloride, hydrobromide, hydrochloride, hydroxynaphthoate, iodide, isothionate, lactate, lactobionate, laurate, malate, maleate, malseate, mandelate, meglumine, mesylate, mesviate, methylbromide, methylnitrate, methylsulfate, mucate, napsylate, nitrate, oleate, oxalate, palmitate, pamoate, pantothenate, phosphate, polygalacturonate, procane, salicylate, stearate, subacetate, succinate, sulfate, tannate, tartrate, teoclate, tosylate, trifluoroacetate, trifluoromethane sulfonate, and valerate.

Certain compounds of the invention may possess one or more chiral centers and may thus exist in optically active forms. Likewise, when the compounds contain an alkenyl or alkenylene group there exists the possibility of cis- and trans-isomeric forms of the compounds. The R- and S-isomers and mixtures thereof, including racemic mixtures as well as mixtures of cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods. For example, a chiral column may be used such as those sold by Daicel Chemical Industries identified by the trademarks:

CHIRALPAK AD, CHIRALPAK AS, CHIRALPAK OD, CHIRALPAK OJ, CHIRALPAK OA, CHIRALPAK OB, CHIRALPAK OC, CHIRALPAK OF, CHIRALPAK OG, CHIRALPAK OK, and CHIRALPAK CA-1.

By another conventional method, a racemic mixture may be reacted with a single enantiomer of some other compound. This changes the racemic form into a mixture of diastereomers. These diastereomers, because they have different melting points, different boiling points, and different solubilities can be separated by conventional means, such as crystallization.

Prodrugs are derivatives of the compounds of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy) alkyl esters or ((alkoxycarbonyl)oxy)alkyl esters. Particularly preferred esters to use as prodrugs are; methyl, ethyl, propyl, isopropyl, n-butyl, isobutyl, morpholinoethyl, and N,N-diethylglycolamido.

N,N-diethylglycolamido ester prodrugs may be prepared by reaction of the sodium salt of a compound of Formula I (in a medium such as dimethylformamide) with 2-chloro-N,N-diethylacetamide (available from Aldrich Chemical Co., Milwaukee, Wis. USA; Item No. 25,099-6).

Morpholinylethyl ester prodrugs may be prepared by reaction of the sodium salt of a compound of Formula I (in a medium such as dimethylformamide) 4-(2-chloroethyl)morpholine hydrochloride (available from Aldrich Chemical Co., Milwaukee, Wis. USA, Item No. C5,220-3). For example, prodrugs may be prepared by reaction of the sodium salt for a compound of Formula I with;

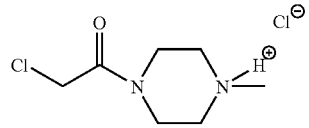

and sodium iodide to provide the ester prodrug pendent group

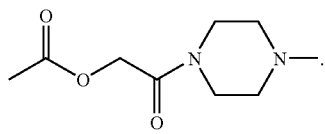

Also, lower alkyl (viz., $C_1$-$C_8$) ester prodrugs may be prepared by conventional means such as reacting the sodium or potassium salt (derived by forming the salt of any acidic compound of the invention; viz., reaction of a base such as KOH with an acidic group such as —CO$_2$H) of a compound of Formulae I with an alkyl iodide such as methyl iodide, ethyl iodide, n-propyl iodide, isopropyl iodide.

Pharmaceutical Formulations containing the Novel Compounds of the Invention:

Pharmaceutical formulations of the invention are prepared by combining (e.g., mixing) a therapeutically effective amount of the compound of the invention (compounds of Formula I) together with a pharmaceutically acceptable carrier or diluent. The present pharmaceutical formulations are prepared by known procedures using well-known and readily available ingredients.

In making the compositions of the present invention, the compounds of the invention will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the compound. The compounds of the present invention are preferably formulated prior to administration.

The compounds of the invention may also be delivered by suitable formulations contained in a transderm patch. Alternatively, the compounds of the invention may be delivered to a patient by sublingual administration.

For the pharmaceutical formulations any suitable carrier known in the art can be used. In such a formulation, the carrier may be a solid, liquid, or mixture of a solid and a liquid. Solid form formulations include powders, tablets and capsules. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

In powders the carrier is a finely divided solid which is in admixture with the finely divided Active Ingredient. In tablets a compound of the invention I is mixed with a carrier having the necessary binding properties in suitable proportions and compacted in the shape and size desired. The powders and tablets preferably contain from about 1 to about 99 weight percent of the compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The Active Ingredient may be dissolved or suspended in a pharmaceutically acceptable carrier, such as sterile water, sterile organic solvent or a mixture of both. The compounds can often be dissolved in a suitable organic solvent, for instance aqueous propylene glycol. Other compositions can be made by dispersing the finely divided compounds of the invention in aqueous starch or sodium carboxymethyl cellulose solution or in a suitable oil.

Methods of Using the Compounds of the Invention:

Many disease states are benefited by treatment with the compounds of Formula I include, but are not limited to: disease states characterized by: abnormal calcium regulation, abnormal cell proliferation, abnormal cell differentiation, abnormal immune response, abnormal dermatological conditions, neurodegenerative condition, inflammation, vitamin D sensitivity, and/or hyperproliferative disorders.

Specific disease states benefited by treatment of the compounds of Formula I include, but are not limited to: Acne, Actinic keratosis, Alopecia, Alzheimer's disease, Benign prostatic hyperplasia, Bladder cancer, Bone maintenance in zero gravity, Bone fracture healing, Breast cancer, Chemoprovention of Cancer, Crohn's disease, Colon cancer, Type I diabetes, Host-graft rejection, Hypercalcemia, Type II diabetes, Leukemia, Multiple sclerosis, Myelodysplastic syndrome, Insufficient sebum secretion, Osteomalacia, Osteoporosis, Insufficient dermal firmness, Periodontal disease, Insufficient dermal hydration, Psoriatic arthritis, Prostate cancer, Psoriasis, Renal osteodystrophy, Rheumatoid arthritis, Scleroderma, Skin cancer, Systemic lupus, rythematosus, Skin cell damage from mustard vesicants, Ulcerative colitis, Vitiligo, and Wrinkles.

Particularly preferred is the treatment of psoriasis and/or osteoporosis by administration to a mammal (including a human) of a therapeutically effective amount of compounds of Formula I. By "pharmaceutically effective amount" it is meant that quantity of pharmaceutical agent corresponding to Formula I which prevents, removes or reduces the deleterious effects of a disease state in mammals, including humans.

The specific dose of a compound administered according to this invention to obtain therapeutic or prophylactic effects will, of course, be determined by the particular circumstances surrounding the case, including, for example, the compound administered, the route of administration and the condition being treated. Typical daily doses will contain a pharmaceutically effective amount typically in the range of from about 0.0001 mg/kg/day to about 50 mg/kg/day of body weight of an active compound of this invention. Preferably the dose of compounds of the invention will be from 0.0001 to 5 mg/kg/day of body weight.

Preferably compounds of the invention or pharmaceutical formulations containing these compounds are in unit dosage form for administration to a mammal. The unit dosage form can be a capsule or tablet itself, or the appropriate number of any of these. The quantity of Active Ingredient in a unit dose of composition may be varied or adjusted from about 0.0001 to about 1000 milligrams or more according to the particular treatment involved. It may be appreciated that it is necessary to make routine variations to the dosage depending on the age and condition of the patient. Dosage will also depend on the route of administration. The compounds of the invention may be administered by a variety of routes including oral, aerosol, rectal, transdermal, sublingual, subcutaneous, intravenous, intramuscular, and intranasal. Particularly preferred is the treatment of psoriasis with an ointment type formulation containing the compounds of the invention. The ointment formulation may be applied as needed, typically from one to 6 times daily.

Treatment of psoriasis is preferably done with topical application by a formulation in the form of a cream, oil, emulsion, paste or ointment containing a therapeutically effective amount of a compound of the invention. The formulation for topical treatment contains from 0.5 to 0.00005 weight percent, preferably from 0.05 to 0.0005 weight percent, and most preferably from 0.025 to 0.001 of a Active Ingredient.

For example, two semisolid topical preparations useful as vehicles for VDR modulators in treatment and prevention of psoriasis are as follows:

Polyethylene Glycol Ointment USP (p. 2495)

Prepare Polyethylene Glycol Ointment as follows:

| | |
|---|---|
| Polyethylene Glycol 3350 | 400 g. |
| Polyethylene Glycol 400 | 600 g. |
| To make | 1000 g. |

Heat the two ingredients on a water bath to 65° C. Allow to cool, and stir until congealed. If a firmer preparation is desired, replace up to 100 g of the polyethylene glycol 400 with an equal amount of polyethylene glycol 3350.

Hydrophilic Ointment USP (p. 1216)
Prepare Hydrophilic Ointment as follows:

| | |
|---|---|
| Methylparaben | 0.25 g. |
| Propylparaben | 0.15 g. |
| Sodium Lauryl Sulfate | 10 g. |
| Propylene Glycol | 120 g. |
| Stearyl Alcohol | 250 g. |
| White Petrolatum | 250 g. |
| Purified Water | 370 g. |
| To make about | 1000 g. |

The Stearyl Alcohol and White Petrolatum are melted on a steam bath, and warmed to about 75° C. The other ingredients, previously dissolved in the water are added, warmed to 75° C., and the mixture stirred until it congeals.

For each of the above formulations the Active Ingredient is added during the heating step in an amount that is from 0.5 to 0.00005 weight percent, preferably from 0.05 to 0.0005 weight percent, and "USP" most preferably from 0.025 to 0.001 weight percent of the total ointment weight. (Source:— United States Pharmacopoeia 24, United States Pharmacopeial Convention, 1999)

Conventional therapy for osteoporosis includes; (i) estrogens, (ii) androgens, (iii) calcium supplements, (iv) vitamin D metabolites, (v) thiazide diuretics, (vi) calcitonin, (vii) bisphosphonates, (viii) SERMS, (ix) fluorides and (x) Parathyroid hormone (PTH) (see, Harrison's Principles of Internal Medicine, 13$^{th}$ edition, 1994, published by McGraw Hill Publ., ISBN 0-07-032370-4, pgs. 2172-77; the disclosure of which is incorporated herein by reference). Any one or a combination of these conventional therapies may be used in combination with the method of treatment using compounds of Formula I as taught herein. For example, in a method of treating osteoporosis, the vitamin D receptor modulator compounds of the invention may be administered separately or simultaneously with a conventional therapy. Alternatively, the vitamin D receptor modulator compounds of the invention may be combined with conventional therapeutic agents in a formulation for treatment of osteoporosis such as set out below:

A formulation for treating osteoporosis comprising:
Ingredient (A1): a vitamin D receptor modulator represented by Formula (I), or a pharmaceutically acceptable salt or prodrug derivative thereof;
Ingredient (B1):
one or more co-agents that are conventional for treatment osteoporosis selected from the group consisting of: estrogens, androgens, calcium supplements, vitamin D metabolites, thiazide diuretics, calcitonin, bisphosphonates, SERMS, fluorides, and PTH
Ingredient (C1): optionally, a carrier or diluent.

Typically useful formulations are those wherein the weight ratio of (A1) to (B1) is from 10:1 to 1:1000 and preferably from 1:1 to 1:100.

Combination Therapy for Psoriasis:

Conventional therapy for psoriasis includes topical glucocorticoids, salicylic acid, crude coal tar, ultraviolet light, and methotrexate (see, Harrison's Principles of Internal Medicine, 13$^{th}$ edition, 1994, published by McGraw Hill Publ., ISBN 0-07-032370-4, pgs. 2172-77). Any one or combination of these conventional therapies may be used in combination with the method of treatment using compounds of Formula I as taught herein. For example, in a method of treating psoriasis, the vitamin D receptor modulator compounds of the invention (e.g., as defined by Formula I) may be topically administered separately or simultaneously with a conventional therapy. Alternatively, the vitamin D receptor modulator compounds of the invention may be combined with conventional therapeutic agents in a topically applied formulation for treatment of psoriasis such as set out below:

A formulation for treating psoriasis comprising:
Ingredient (A2): a vitamin D receptor modulator represented by Formula (I), or a pharmaceutically acceptable salt or prodrug derivative thereof;
Ingredient (B2):
one or more co-agents that are conventional for treatment psoriasis selected from the group consisting of: topical glucocorticoids, salicylic acid, or crude coal tar.
Ingredient (C2): optionally, a carrier or diluent.

Typically useful formulations are those wherein the weight ratio of (A2) to (B2) is from 1:10 to 1:100000 and preferably from 1:100 to 1:10000.

Experimental Results:

TABLE 2

Summary of Experimental Results

| Test Cmpd.[1] | RXR-VDR heterodimer[2] $EC_{50}$ (nM) | OCN Promoter[3] $EC_{50}$ (nM) | Kera. Prolif. $IC_{50}$ (nM)[4] |
|---|---|---|---|
| Ex. 1 | 1117 | 376 | |
| Ex. 2 | 73 | 289 | >1000 |
| Ex. 3 | 701 | 1642 | |
| Ex. 4 | 700 | 1174 | |
| Ex. 5 | 37 | 8 | >1000 |
| Ex. 6 | 5 | | 36 |
| Ex 7 | 177 | | >1000 |
| Ex 8 | 117 | | >1000 |
| Ex 9 | 150 | | >1000 |

Expalnation of Table 2 column numerical superscripts:
[1]Test Compound numbers refer to the products of the corresponding Example Nos. that is, compounds within the scope of the invention.
[2]The RXR-VDR heterodimerization (SaOS-2 cells) test is described in the "Assay" section of the Description, infra.
[3]The OCN Promoter test is described in the "Assay" section of the Description, infra.
[4]The keratinocyte proliferation assay is described in the "Assay" secion of the Description, infra.

Assay Methods

Use of the Assay Methods:

The evaluation of the novel compounds of the invention for osteoporosis and other related diseases is done using a plurality of test results. The use of multiple assays is beneficial since it is preferred that the combined properties of (i) high activity for the vitamin D receptor, and (ii) prevention of hypercalcemia be achieved to effect of treating diseases, which are also aspects of this invention. Some of the tests described below are believed related to other tests and measure related properties of compounds. Consequently, a compound may be considered to have utility in the practice of the invention if it meets at least one preferably two or more, if not all, of the acceptance criteria for the above described tests.

The evaluation of the novel compounds of the invention for psoriasis is done using the Keratinocyte Proliferation Assay in combination with other assays that measure inhibition of IL-2 production and stimulation of IL-10 production in peripheral blood mononuclear cells (PBMCs).

Brief Description, Utility and Acceptance Criteria for the Assay Methods

1. The RXR-VDR heterodimerAssay:

This assay provides the VDR activity of a test compound. It is desirable to have low EC50 values for a compound in this assay. The lower the EC50 value, the more active the compound will be as a VDR agonist. Desired assay results are EC50 values less than or equal to 600 nM. Preferred assay results are less than 250 nM, and most preferably less than 150 nM.

(1) Materials and Method for RXR-VDR Heterodimerization Assay Transfection Method: Reagents: FuGENE 6 Transfection Reagent (Roche Cat # 1 814 443); Growth Media: D-MEM High Glucose (Gibco BRL Cat # 11054-020), 10% heat inactivated FBS (Gibco BRL Cat # 10092-147), 1% antibiotic-antimycotic (Ab-Am); (Gibco BRL Cat # 15240-062).

Cells: Grow SaOS-2 cells in T-150 $cm^2$ culture flasks in growth media keeping the density at $5$-$6 \times 10^5$ cells/ml. Passage cells 1:3 twice a week. Add Trypsin EDTA (Gibco BRL Cat # 25300-020) and incubate. Resuspend cells in plating media and transfer into growth media.

Wash Media: HBSS Low Glucose Without Phenol Red (Gibco BRL Cat # 14175-095), 1% Ab-Am. Plating Media: D-MEM Low Glucose Without Phenol Red (Gibco BRL Cat # 11054-020), 1% Ab-Am; D-MEM; 10% Stripped FBS (Hyclone Cat# SH30068.03 Lot # AHM9371).

Transfection/Treatment Media: D-MEM Low Glucose Without Phenol Red only; T-150 $cm^2$ culture flask: Use Corning Coastar T-150 $cm^2$ culture flask (Cat #430825) to grow the cells.

Luciferase Assay Reagent: Use Steady-Glo Luciferase Reagent from Promega (Cat # E2550) Consists of: E2533 Assay Substrate, lypholized product and E2543 Assay Buffer. Thaw at room temperature and store.

Cell Harvesting/Count: Aspirate media from culture flask, rinse cells with HBSS and aspirate. Add trypsin and incubate. When cells appear detached, resuspend cells in growth media. Transfer into a new flask with fresh growth media for passaging the cells. Plate 96 well plates and two extra plates. Mix the cell suspension using pipette. To count the cells using a Hematocytometer.

Plate seeding: Use plating media 10% Stripped FBS in D-MEM Low Glucose, without Phenol Red, 1% Ab-Am. Plate 14 plates @ 165 µl/well. In sterile flask add cell suspension to plating media and mix. Add cells/well. Place the cells in the incubator. Cells should be about 75% confluent prior to transfection. DAY 2: Transfection: Step 1, DNA and Media: Add plain DMEM media to tubes for mixing the DNA; add the Reporter gene pFR-LUC; and add the Gal-4-RXR-DEF and VP16-VDR-LBD. Step 2, FuGENE and Media: Prepare plain DMEM media in a tubes for mixing FuGENE, add FuGENE 6 Transfection Reagent, and incubate. Step 3, FuGENE, DNA and Media Complex: Add FuGENE Media complex from step 2 to DNA Media complex from step 1 and incubate. Step 4, FuGENE, DNA and Media Complex to 96 well plate: Add FuGENE-DNA-Media complex from step 3 to each plate. Incubate.

Day 3: Dosing: Treatment preparation. Allow for transfection time.

Make a stock solution of the compounds in DMSO and vortex until all the compounds have been dissolved. Further dilute in D-MEM (Low Glucose—without Phenol Red) Add compounds in quadruplicate to give desired final volume then incubate.

Day 4: Luciferase Assay: Read the plates after drug treatment. Remove part of media from all the wells and leave remainder. Add Steady-Glo Luciferase Reagent mixture/wells and incubate. Count each well using a Luminescence counter, Top Count NXT by Packard preferably set a delay between plates to reduce the background.

The Caco-2 Cell Co-Transfection Assay:

The Caco-2 cell assay is an indicator for the undesirable condition of hypercalcemia. This co-transfection assay is a surrogate assay for in vivo calcemic activity of VDR ligands. It is desirable to have high EC50 values for a test compound in this assay. The higher the EC50 values for a compound the less calcemic it will be in vivo. Desired assay results are EC50 greater than or equal to 300 nM. Preferred assay results are greater than 1000 nM.

Caco-2 cells, grown in phenol red free, DMEM (Invitrogen, Carlsbad, Calif.) containing 10% charcoal-stripped FBS (Hyclone, Logan, Utah), are transfected with Fugene 6 reagent (Roche Diagnostics, Indianapolis, Ind.). Cells (5000/well) are plated 18 h before transfection in a 96 well plate. The cells are transfected with Gal-4-responsive reporter pFRLuc (150 ng, Stratagene, La Jolla Calif.) and the receptor expression vector pGal-4-VDR-LBD (10 ng), along with Fugene 6 reagent (0.2 µl/well). The DNA-Fugene complex is formed by incubating the mixture for 30 m at room temperature. The cells are transfected in triplicate for 5 h, and treated with various concentrations of VDR ligands (from 0.01 nM to 10,000 nM concentration range) 18 h post-transfection. The luciferase activity is quantified using Steady-Glo reagent kit (Promega, Madison, Wis.) as per manufacturer's specifications.

The OCN (osteocalcin) Promoter Assay

The OCN Promoter Assay is an indicator and marker for osteoporosis. Desired assay results are EC50 less than or equal to 325 nM. Preferred assay results are less than 50 nM.

The activation of osteocalcin by VDR ligands is evaluated in a rat osteoblast-like cell line RG-15 (ROS17/2.8) stably expressing rat osteocalcin promoter fused with luciferase reporter gene. The stable cell lines are established as reported before (Activation of Osteocalcin Transcription involves interaction of protein kinase A- and Protein kinase C-dependent pathways. Boguslawski, G., Hale, L. V., Yu, X.-P., Miles, R. R., Onyia, J. E., Santerre R. F., Chandrasekhar, S. *J. Biol. Chem.* 275, 999-1006, 2000). Confluent RG-15 cells maintained in DMEM/F-12 medium (3:1) containing 5% FBS, 300 µg/ml G418 and at 37° C. under 5% $CO_2$/95% air atmosphere are trypsinized (0.25% trypsin) and plated into white opaque 96-well cell culture plates (25000 cells/well). After 24 h, cells (in DMEM/F-12 medium+2% FBS) are treated with various concentrations of compounds, dissolved in DMSO. The final DMSO concentration remains at 0.01% (v/v). After 48 h treatment, the medium is removed, cells are lysed with 50 µl of lysis buffer (From Luciferase reporter assay system, Roche Diagnostics, Indianapolis, Ind.) and then assayed for luciferase activity using the Luciferase Reporter Gene Assay kit from Boehringer Mannheim as per manufacturer's specifications.

The Mouse Hypercalcemia Assay

The Mouse Hypercalcemia Assay is a six day hypercalcemia test for toxicity and selectivity. Acceptable test results are levels greater than 30 μg/kg/day. Preferred assay results are levels greater than 300 μg/kg/day.

Weanling, virus-antibody-free, five to six weeks old female DBF mice (Harlan, Indianapolis, Ind.) are used for all the studies. Animals are allowed to acclimate to local vivarium conditions for 2 days. Mice are maintained on a 12 h light/dark cycle at 22° C. with ad lib access to food (TD 5001 with 1.2% Ca and 0.9% P. Teklad, Madison, Wis.) and water. The animals then are divided into groups with 4-5 mice per group. Different doses of test compounds prepared in 10% ethanol and 90% sesame oil, or in an aqueous suspension of sodium lauryl sulfate and CMC (the latter formulation for acidic compounds) are administered to mice orally via gavage for 6 days. $1\alpha$-$25(OH)_2D_3$ 0.5 μg/kg/d was also given to one group of mice as the positive control. Serum ionized calcium is evaluated at 6 hs after the last dosing under isoflurane anesthesia by Ciba-Corning Ca++/PH Analyzer, (Model 634, Chiron Diagnostics Corp., East Walpole, Mass.). Raw data of group differences is assessed by analysis of variance (ANOVA) using Fisher's protected least significant difference (PLSD) where the significance level was $P<0.05$. The highest dose that did not cause hypercalcemia, as defined by the 97.5% reference distribution of the control population, is considered "the no effect level".

The Keratinocyte Proliferation Assay

This Assay is indicative for the treatment of psoriasis. An acceptable test result is IC50 value of less than or equal to 300 nM. Preferred assay results are IC50 values of less than 100 nM.

KERtr cells (Human skin keratinocyte) are transformed with a retrovirus vector, obtained from ATCC, then are plated in 96-well flat-bottomed plates (3000 cells/well) in 100 μl keratinocyte serum free medium supplemented with bovine pituitary extract in the absence of EGF (Life Technologies, Rockville, Md.) and are incubated at 37° C. for two days. The cells are treated with various concentrations of VDR ligands (ten-fold serial dilution from 10,000 nM to 0.1 nM in triplicate), dissolved in 100 μl keratinocyte serum free medium supplemented with bovine pituitary extract in the absence of EGF and are incubated at 37° C. for 72 h. BrdU (5-bromo-2'-deoxyuridine) incorporation is analyzed as a measure of DNA replication (Cell proliferation ELISA kit, Roche Diagnostics, Indianapolis, Ind.) and absorbance is measured at 405 nm. Potency values ($IC_{50}$) values were determined as the concentration (nM) of compound that elicited a half-maximal response.

The IL-10 induction Assay

This is an in vitro efficacy assay for psoriasis, abscess and adhesion. Psoriasis involves both keratinocytes and immune cells. IL-10 is a unique cytokine because it is anti-inflammatory and immunosuppressive. This assay tells us whether a VDRM is able to function as an agonist in PBMCs (primary blood mononuclear cells) or not. A lower EC50 value is desirable in this assay since a compound with a lower EC50 value will be a better agonist in PBMCs. An acceptable test result is an EC50 value of less than 200 nM. Preferred assay results are EC50 values of less than 100 nM.

Isolation of Peripheral Blood Mononuclear Cells (PBMCs):

Collect 50 ml of human blood and dilute with media, RPMI-1640. Add diluted blood to sterile tubes with ficol. Centrifuge the tubes. Discard the top layer and collect the cells from middle layer. Divide all cells into four tubes and add media. Centrifuge; aspirate off media and resuspend the cells. Collect all cells. Centrifuge at 1200 pm for 10 m. Resuspend the cells in RPMI-1640 with 2% FBS and then count cells.

Stimulation of PBMC: Prepare TPA in DMSO. Dissolve PHA in water. Plate TPA/PHA treated PBMCs in well plates. Incubate the cells.

Treatment: Prepare all compound dilutions in plain RPMI-1640 media. Add diluted compound and incubate. Sample Collection and assay: Remove all the cells by centrifugation and assay the supernatant for IL-10 by immunoassay using anti-human IL-10 antibody coated beads, as described by the manufacturer (Linco Research Inc., St. Charles, Mo.).

Other Compound Assay Standards

An alternative measure of the therapeutic index (bone efficacy vs hypercalcemia) of compounds of the invention for treatment of osteoporosis is a numerical ratio calculated as follows:

> Dose Threshold needed to induce hypercalcemia divided by Dose Threshold needed for bone efficacy An alternative measure of the therapeutic index (in vivo keratinocyte proliferation vs. hypercalcemia) of compounds of the invention for treatment of psoriasis is a numerical ratio calculated as follows:

> Dose Threshold needed to induce hypercalcemia divided by Dose Threshold needed to induce keratinocyte proliferation For the above ratios, Dose Thresholds are determined from dose response curve data.

The CaT1 (calcium transporter 1) Assay

The CaT1 Assay is an indicator for the undesirable condition of hypercalcemia. The higher the EC50 values for a compound the less calcemic it will be in vivo. Desired assay results are EC50 greater than or equal to 500 nM. Preferred assay results are greater than 1000 nM.

Human colon carcinoma, Caco-2 cells, maintained in DMEM (high glucose with 25 mM Hepes buffer; Invitrogen, Carlsbad, Calif.) supplemented with 10% FBS (Invitrogen, Carlsbad, Calif.), are plated at 5500 cell per well in a 96-well plate in a total volume of 100 μl/well. The cells are kept in the 96-well plate for 6 days to differentiate them to small intestinal cells that express the calcium transporter, CaT1. On day 3 after plating, old media is removed and replaced with fresh media (150 μl/well). On day 6 the old media is removed and the cells are kept in treatment media (180 μl/well) that contained 10% charcoal stripped FBS (Hyclone, Logan, Utah) in DMEM (low glucose, without phenol red; Invitrogen, Carlsbad, Calif.). The cells are treated with various concentrations of VDR ligands (from 0.01 nM to 10,000 nM concentration range) prepared in treatment media (20 μl/well). Twenty hours post-treatment, total RNA is prepared by RNeasy 96 method as described by the manufacturer (Qiagen, Valencia, Calif.). The RNA is reverse transcribed and amplified for human CaT1 and GAPDH (control) messages by quantitative RT-PCR using ABI PRISM 7900HT Sequence Detection System according to manufacturer's instructions (Applied Biosystems, Foster City, Calif.). Optimized primer pairs and probes for human CaT1 and GAPDH genes are obtained commercially (Applied Biosystems, Foster City, Calif.). Each 20 μl quantitative RT-PCR reaction in a 384-well Taqman PCR plate consists of forward and reverse primers (900 nM), Taqman probe (200 nM), total RNA (4 μl form each well of the 96-well culture plate) and 10 μl of Taqman Universal PCR Master Mix (Roche Diagnostics, Indianapolis, Ind.). Reactions are incubated at 48° C. for 30 m followed by 10 m at 95° C. and subjected to 40 cycles of PCR (95° C. for 15 seconds followed by 60° C. for 1 m). GAPDH is used as an internal control and its primer and probe set are obtained commercially (Applied Biosystems, Foster City, Calif.).

The invention claimed is:

1. A compound or a pharmaceutically acceptable salt thereof represented by a formula below:

wherein
R and R' are independently $C_1$-$C_5$ alkyl:
$RP_3$ is selected from: hydrogen or $C_1$-$C_5$ alkyl:
$(L_{P1})$ and $(L_{P2})$, are divalent linking groups independently selected from the group consisting of: a bond, $(CH_2)_m$—CH(OH)—, $(CH_2)_m$—C(Me)(OH)—$(CH_2)_m$ —O—, $(CH_2)_m$—C(R40)(R41)-, and —$(CH_2)_m$—C(O)—, where m is 0-5;
R40 and R41 each is independently hydrogen or $C_1$-$C_5$ alkyl;
$Z_P$ is a branched $C_3$-$C_5$ alkyl
$Z_{XB}$ is selected from: $C_0$-$C_5$ alkyl-$CO_2H$, $C_0$-$C_5$ alkyl-N(R40)(R41) or C(O)($OC_1$-$C_5$alkyl), C(O)N(R40)(R41), N(R42)-($C_1$-$C_5$alkyl)$CO_2H$, and —N(R42)-($C_1$-$C_5$ alkyl)C(O)($OC_1$-$C_5$alkyl):
R42 is H or $C_1$-$C_3$ alkyl;
provided that $Z_{XB}$ is substituted at either the 5 or 6 position of the benzoxazole ring.

2. A compound of claim 1, or a pharmaceutically acceptable salt derivative thereof,
wherein
R and R' are independently methyl or ethyl;
$RP_3$ hydrogen, methyl, or ethyl;
$(L_{P2})$ is a bond, —$CH_2$— or —CH(OH)—;
$Z_P$ is 1,1-dimethylethyl;
$Z_{XB}$ is selected from —$CO_2H$, —N(R40)(R41), N(R41)-($C_1$-$C_5$ alkyl)$CO_2H$, —C(O)N(R40)(R41), —NMe-$CH_2$—C(O)OMe, —NMe-$CH_2$—C(O)OEt, —NMe-$CH_2$—C(O)OiPr, —Nme-$CH_2$—C(O)tBu, —NMe-C(Me)$_2$-C(O)OH, and —$CH_2CO_2H$.

3. A compound according to claim 1 represented by formulae (C1) to (C16) or a pharmaceutically acceptable salt thereof:

-continued

C7)
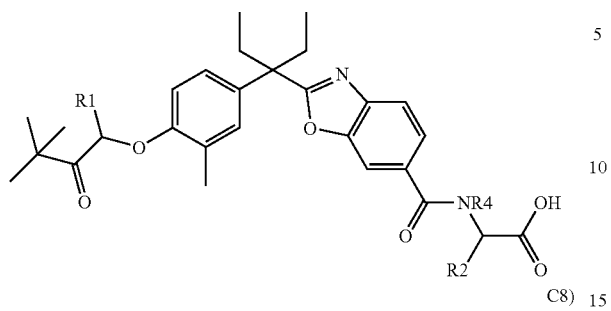

C8)
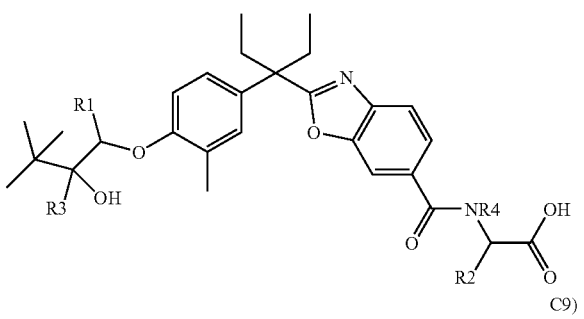

C9)
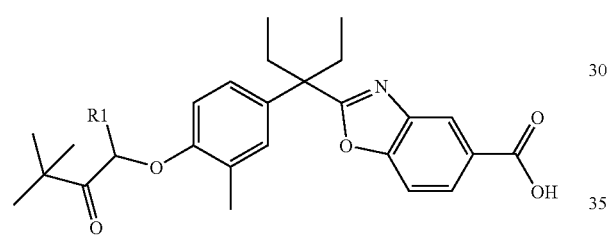

C10)
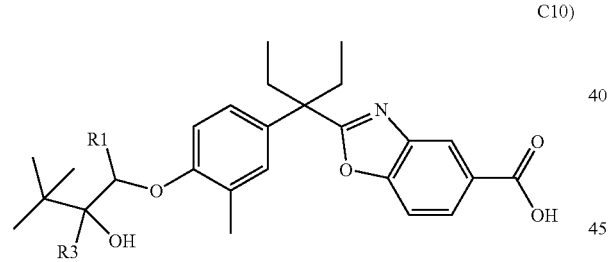

C11)
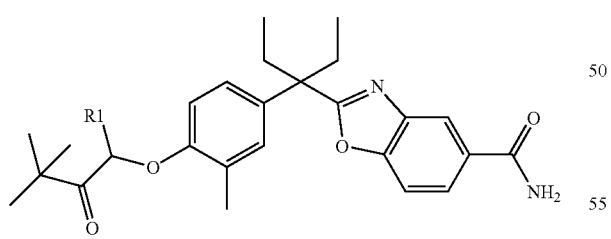

C12)

-continued

C13)
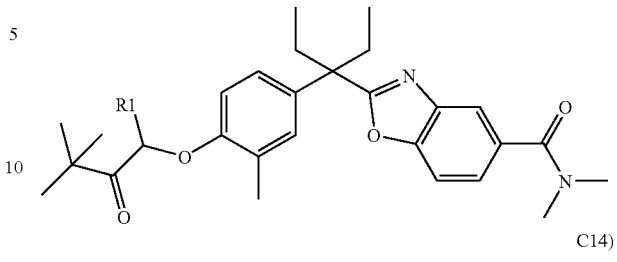

C14)
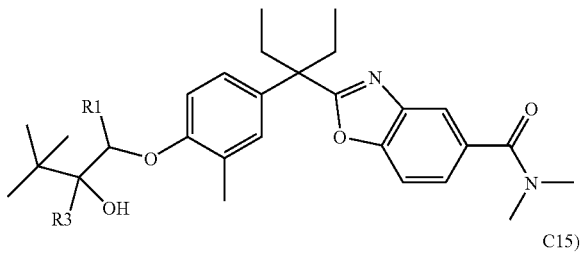

C15)
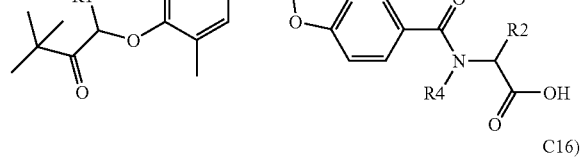

C16)
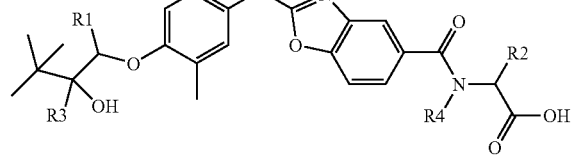

where R1 is H, methyl or ethyl; R2 is H or Me; R3 is H, methyl or ethyl; and R4 is H or methyl.

4. The compounds of claim 3, or pharmaceutically acceptable salts thereof, where R1 is methyl or ethyl and R2 is H or methyl.

5. The compound of claim 3 represented by the structural formula

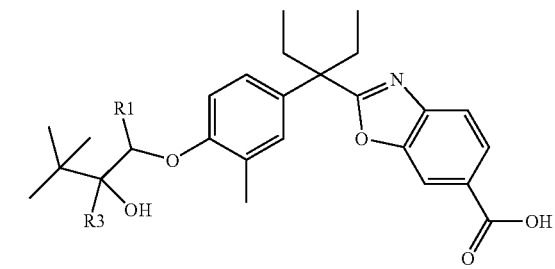

or a pharmaceutically acceptable salt thereof.

6. A compound of claim 3 represented by the structural formula

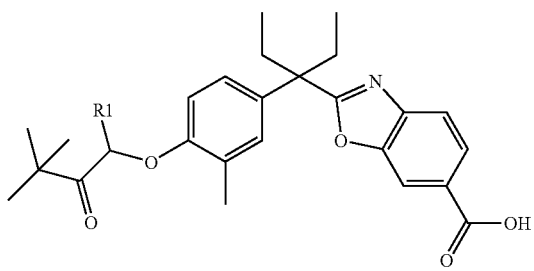

or a pharmaceutically acceptable salt thereof

7. A compound of claim 1 wherein the salt counter-ion is sodium or potassium.

8. A pharmaceutical formulation comprising the compound of claim 1 or a pharmaceutically acceptable salt thereof, with a pharmaceutically acceptable carrier or diluent.

9. A method of treating a mammal for osteoporosis or psoriasis; wherein the method comprises administering a pharmaceutically effective amount of at least one compound according to claim 1, or a pharmaceutically acceptable salt thereof.

10. The method of claim 9 for the treatment of psoriasis.

11. The method of claim 9 for the treatment of osteoporosis.

* * * * *

UNITED STATES PATENT AND TRADEMARK OFFICE
CERTIFICATE OF CORRECTION

PATENT NO. : 7,659,296 B2  Page 1 of 2
APPLICATION NO. : 11/721676
DATED : February 9, 2010
INVENTOR(S) : Quanrong Shen It is certified that error appears in the above-identified patent and that said Letters Patent is hereby corrected as shown below:

Title page, column 1, item (*), please delete "U.S.C. 154(b) by 0 days" and replace with -- U.S.C. 154(b) by 67 days --.

Title page, column 2, item [57] under the title "ABSTRACT", line 2, after "Formula (I)" insert

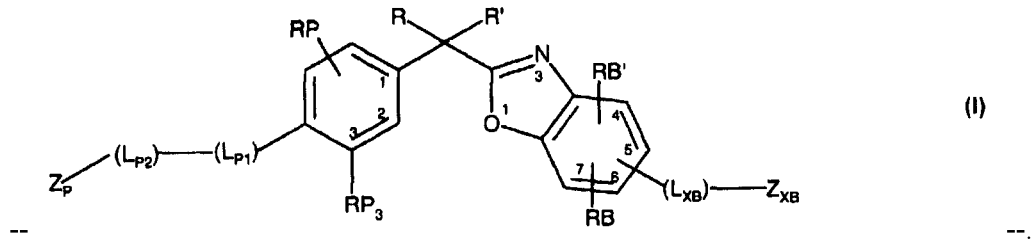

-- --.

Column 39, line 25, in Claim 1, delete "(CH$_2$)$_m$—" and insert -- —(CH$_2$)$_m$— --, therefor.

Column 39, line 16, in Claim 1, delete "—(CH$_2$)$_m$ —O—" and insert -- —(CH$_2$)$_m$—O— --, therefor.

Column 39, line 27, in Claim 1, delete "—C(R40)(R41)-," and insert -- —C(R40)(R41)—, --, therefor.

Column 39, line 32, in Claim 1, delete "alkyl-CO$_2$H," and insert -- alkyl—CO$_2$H, --, therefor.

Column 39, line 32, in Claim 1, delete "alkyl-N" and insert -- alkyl—N --, therefor.

Column 39, line 33, in Claim 1, delete "N(R42)-(C$_1$-C$_5$alkyl)CO$_2$H," and insert -- —N(R42)—(C$_1$-C$_5$alkyl)CO$_2$H, --, therefor.

Column 39, line 34, in Claim 1, delete "—N(R42)-(C$_1$-C$_5$" and insert -- —N(R42)—(C$_1$-C$_5$ --, therefor.

Column 39, line 44, in Claim 2, delete "—CH$_2$—or" and insert -- —CH$_2$— or --, therefor.

Column 39, lines 47-48, in Claim 2, delete "—NMe-CH$_2$—C(O)OMe," and insert -- —NMe—CH$_2$—C(O)OMe, --, therefor.

Column 39, line 48, in Claim 2, delete "—NMe-CH$_2$—C(O)OEt," and insert -- —NMe—CH$_2$—C(O)OEt, --, therefor.

Column 39, lines 48-49, in Claim 2, delete "—NMe-CH$_2$—C(O)OiPr," and insert -- —NMe—CH$_2$—C(O)OiPr, --, therefor.

CERTIFICATE OF CORRECTION (continued)
U.S. Pat. No. 7,659,296 B2

Column 39, line 49, in Claim 2, delete "—NMe-CH$_2$—C(O)OtBu," and insert -- —NMe—CH$_2$—C(O)OtBu, --, therefor.

Column 39, lines 49-50, in Claim 2, delete "—NMe-C(Me)$_2$-C(O)OH," and insert -- —NMe—C(Me)$_2$—C(O)OH, --, therefor.

Column 43, line 15, in Claim 6, delete "thereof" and insert -- thereof. --, therefor.

Signed and Sealed this

Sixth Day of April, 2010

David J. Kappos
*Director of the United States Patent and Trademark Office*

UNITED STATES PATENT AND TRADEMARK OFFICE
CERTIFICATE OF CORRECTION

PATENT NO. : 7,659,296 B2  Page 1 of 1
APPLICATION NO. : 11/721676
DATED : February 9, 2010
INVENTOR(S) : Shen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 152 days.

Signed and Sealed this

Thirtieth Day of November, 2010

David J. Kappos
*Director of the United States Patent and Trademark Office*